(12) United States Patent
Tran et al.

(10) Patent No.: US 7,135,401 B2
(45) Date of Patent: Nov. 14, 2006

(54) METHODS OF FORMING ELECTRICAL CONNECTIONS FOR SEMICONDUCTOR CONSTRUCTIONS

(75) Inventors: Luan C. Tran, Meridian, ID (US); Fred D. Fishburn, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 183 days.

(21) Appl. No.: 10/841,708

(22) Filed: May 6, 2004

(65) Prior Publication Data

US 2005/0250315 A1    Nov. 10, 2005

(51) Int. Cl.
*H01L 21/4763* (2006.01)

(52) U.S. Cl. .................. 438/637; 257/E21.4

(58) Field of Classification Search ........... 438/597, 438/618, 622, 637, 666, 669, 674, 675
See application file for complete search history.

(56) References Cited

U.S. PATENT DOCUMENTS 5,466,639 A    11/1995   Ireland
6,163,067 A    12/2000   Inohara et al.
6,337,267 B1    1/2002   Yang
2003/0000644 A1  1/2003   Subramanian et al.

FOREIGN PATENT DOCUMENTS

DE    102 00 428 A1    4/2003
WO    2005/014951       4/2005

*Primary Examiner*—Scott B. Geyer
(74) *Attorney, Agent, or Firm*—Wells St. John P.S.

(57) ABSTRACT

The invention includes methods for forming electrical connections associated with semiconductor constructions. A semiconductor substrate is provided which has a conductive line thereover, and which has at least two diffusion regions adjacent the conductive line. A patterned etch stop is formed over the diffusion regions. The patterned etch stop has a pair of openings extending through it, with the openings being along a row substantially parallel to an axis of the line. An insulative material is formed over the etch stop. The insulative material is exposed to an etch to form a trench within the insulative material, and to extend the openings from the etch stop to the diffusion regions. At least a portion of the trench is directly over the openings and extends along the axis of the line. An electrically conductive material is formed within the openings and within the trench.

50 Claims, 28 Drawing Sheets

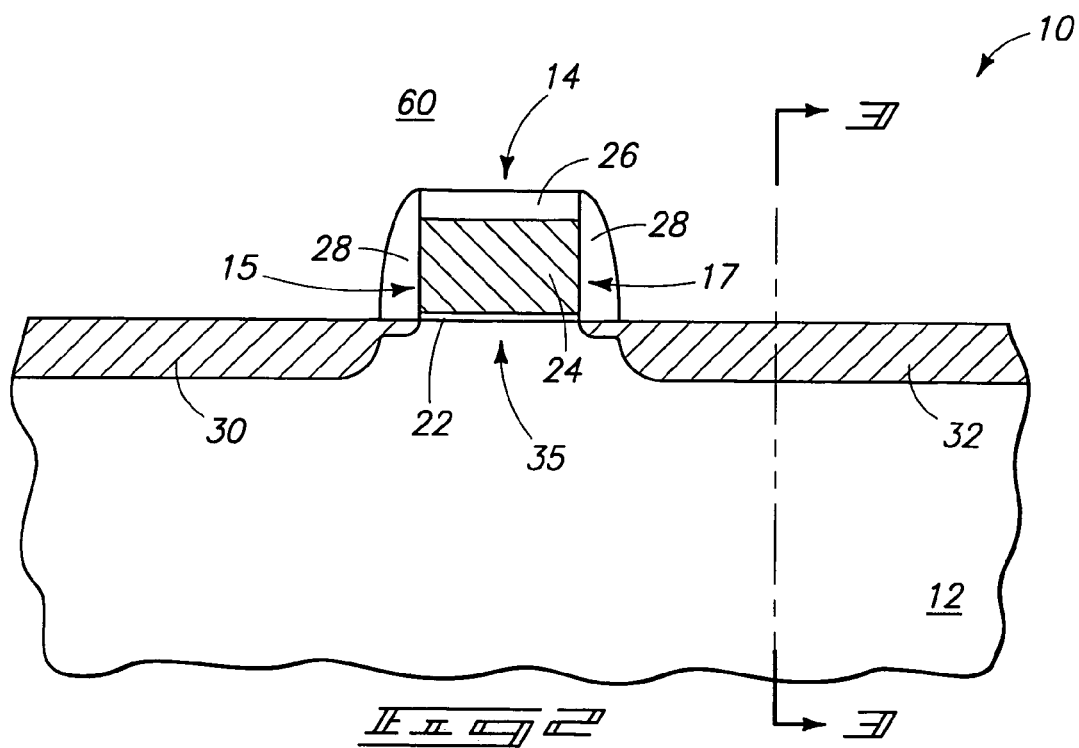
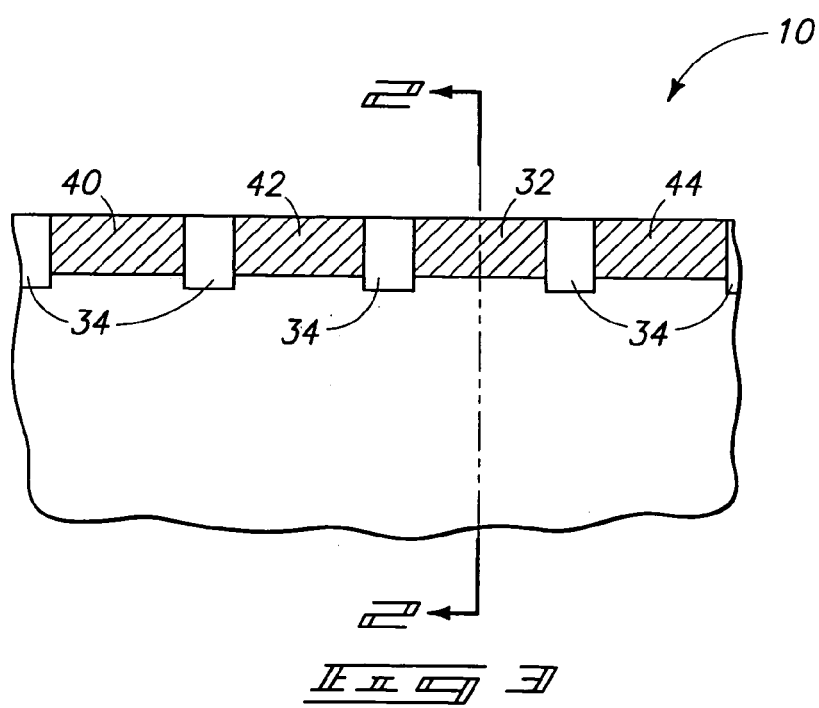

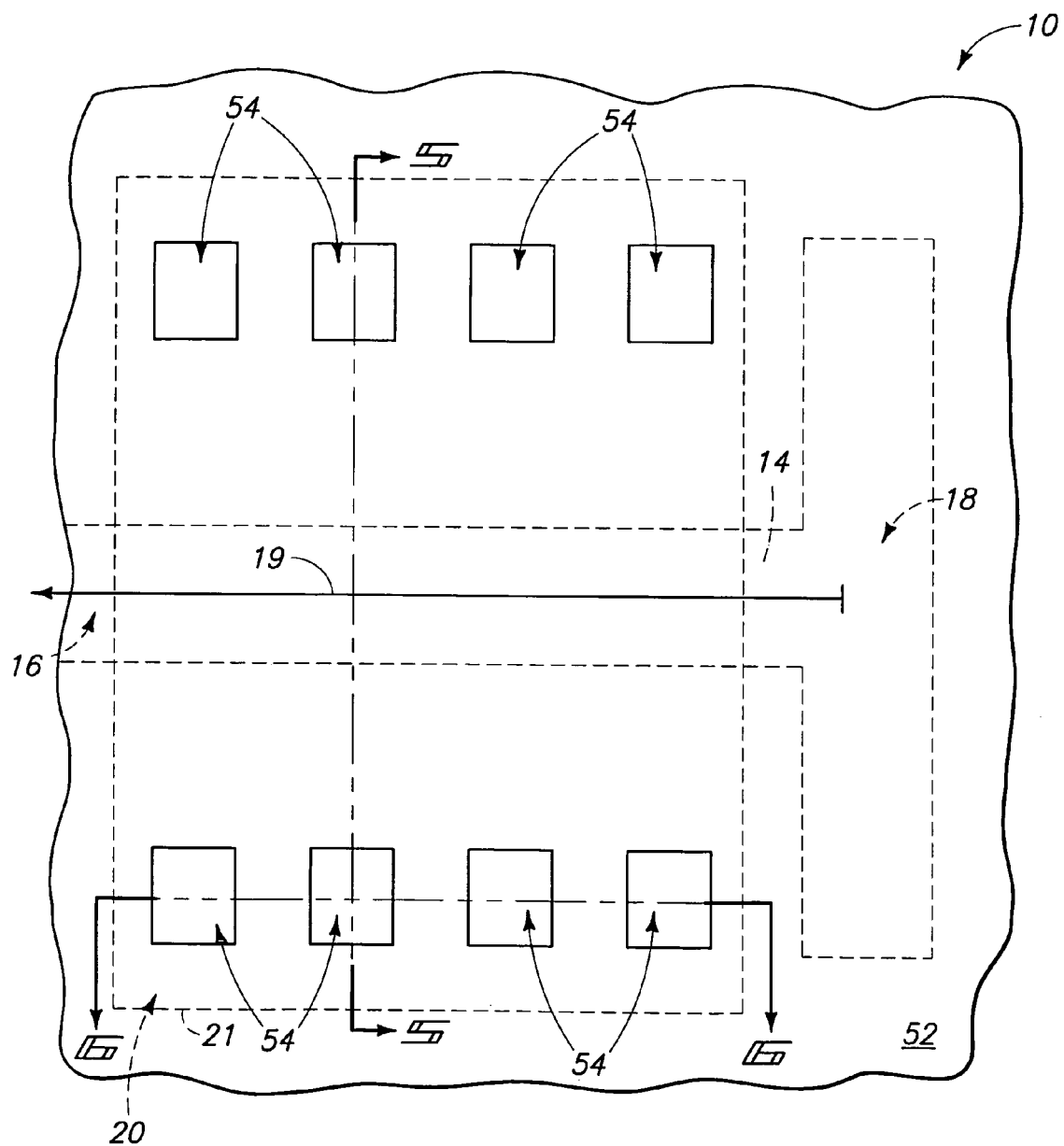

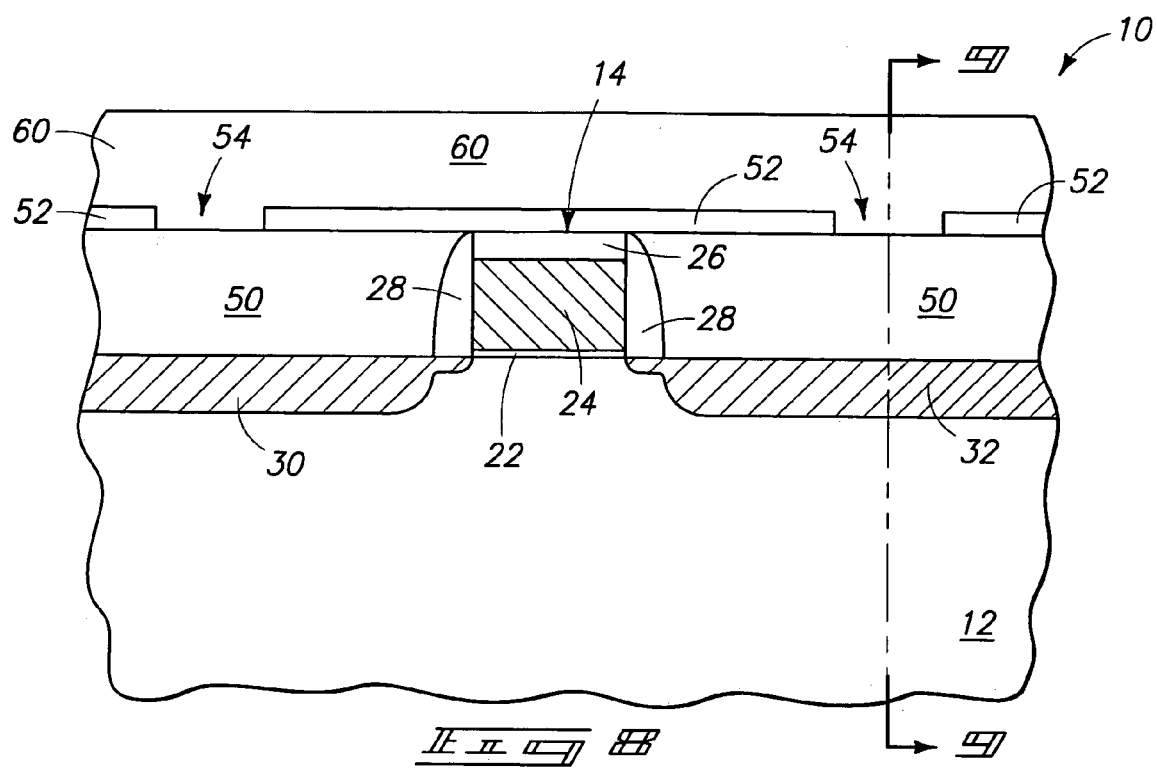
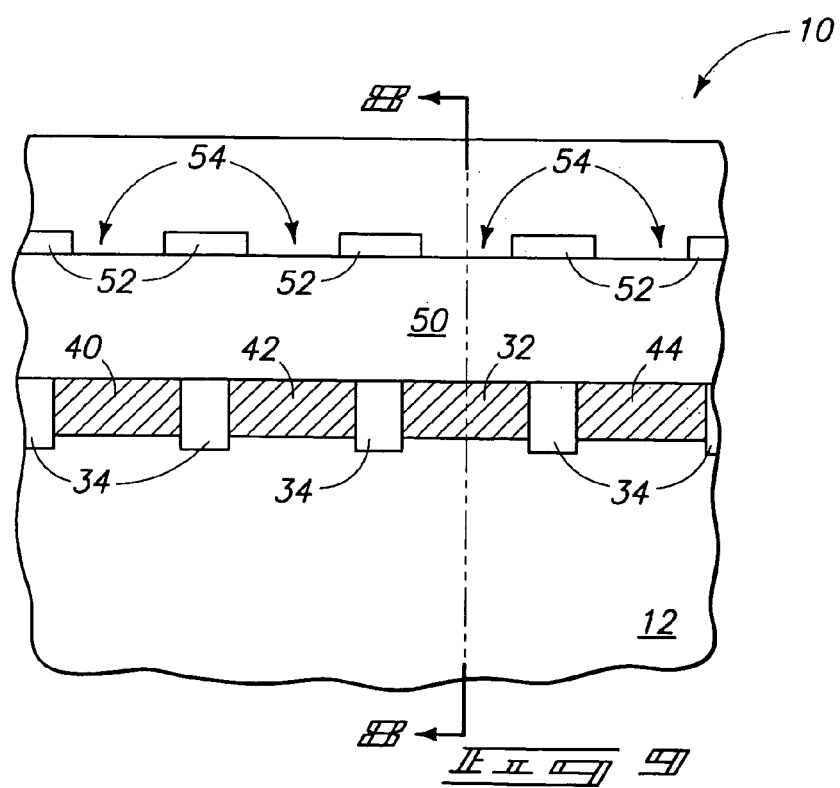

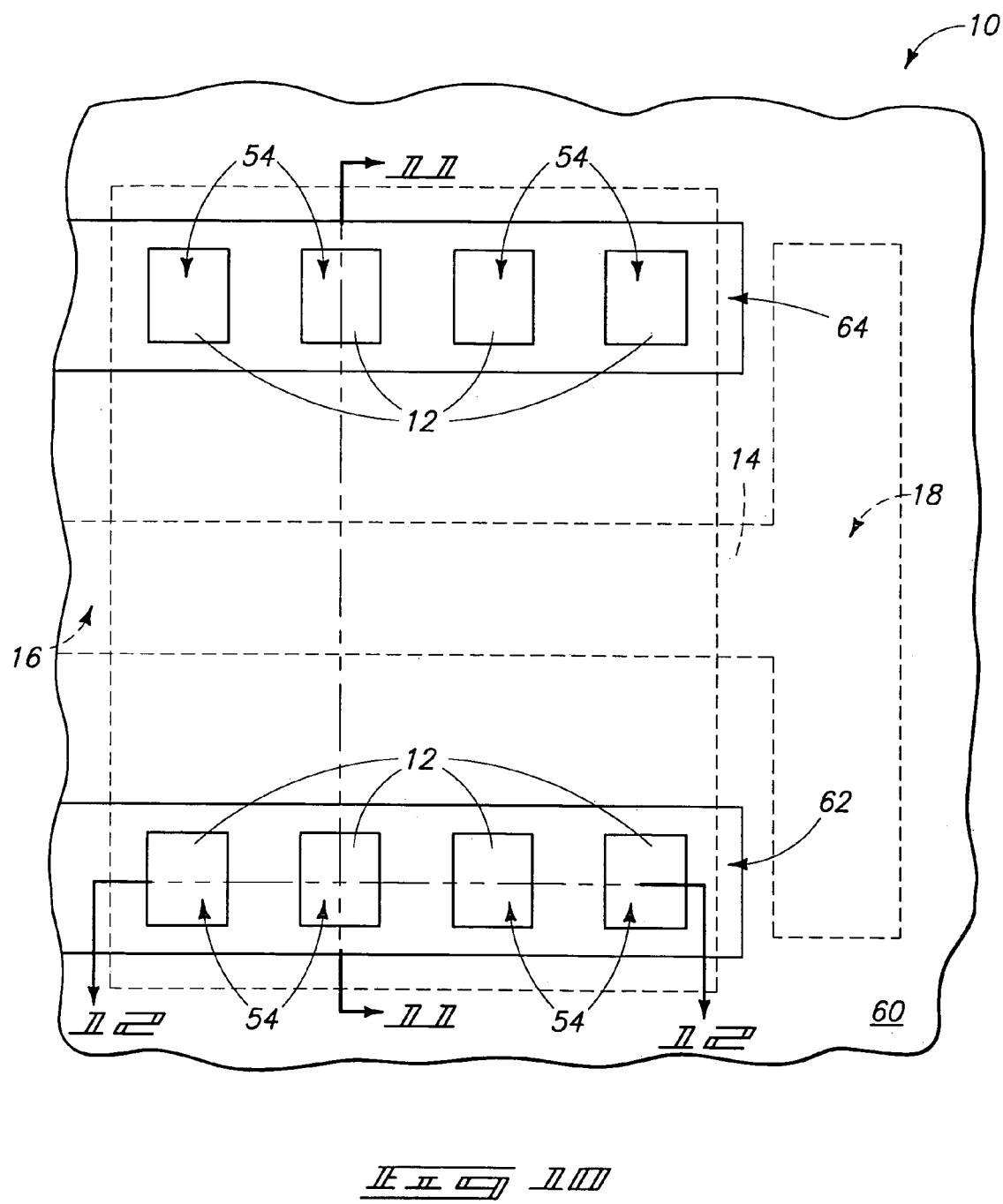

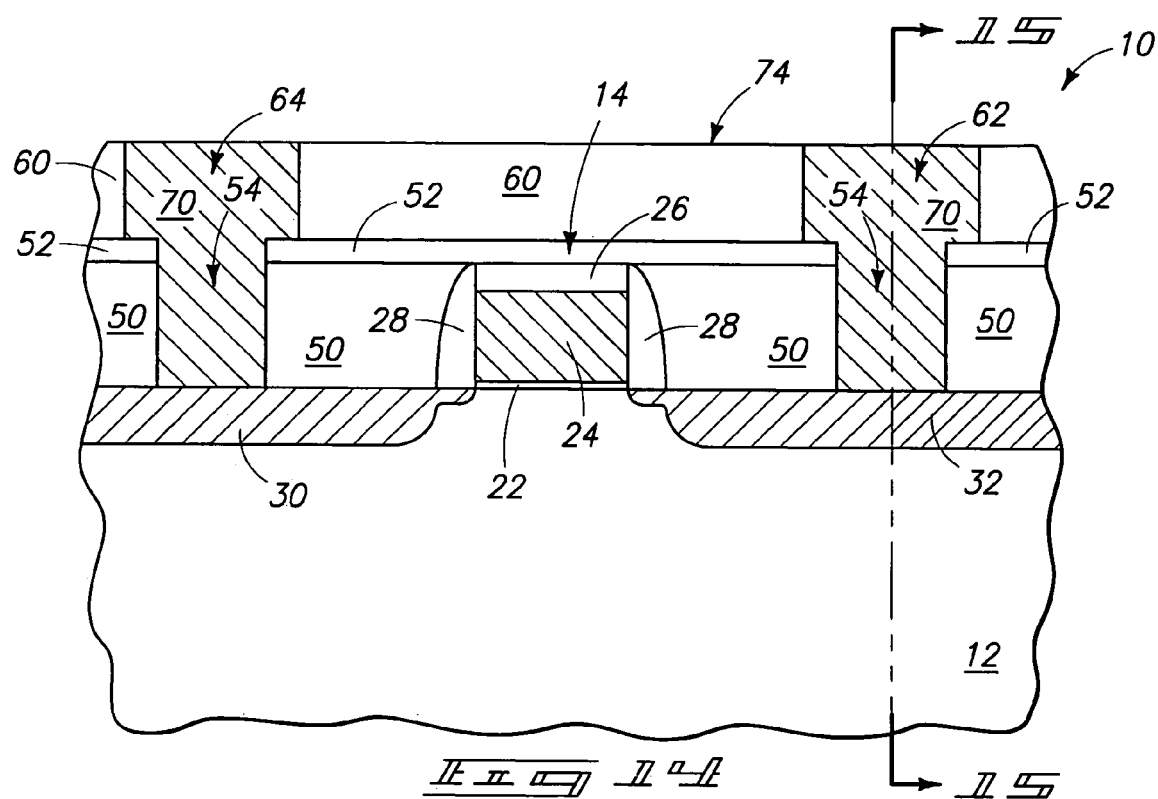
F I G. 14
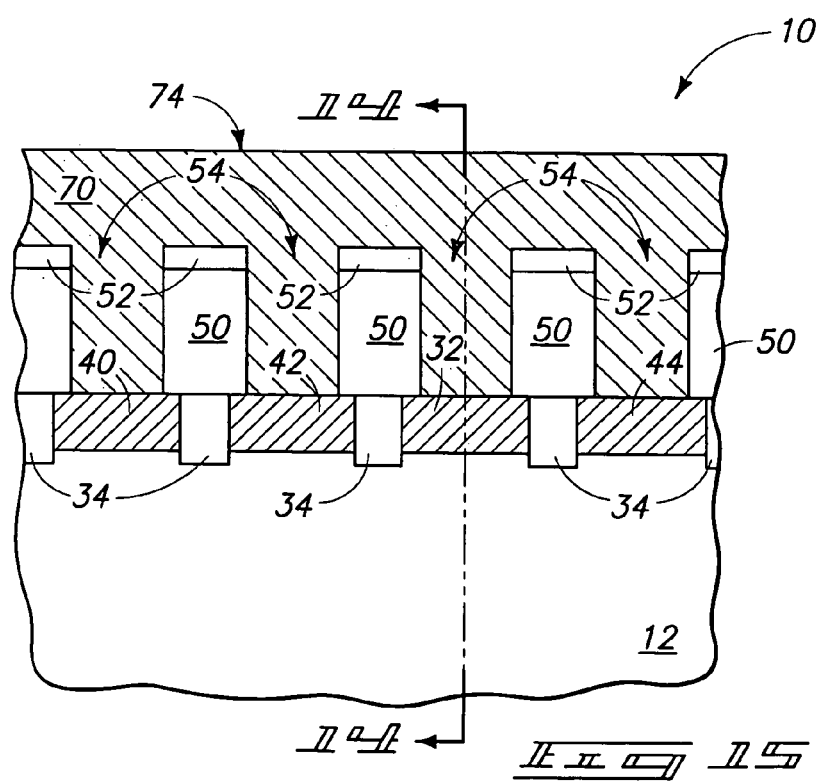
F I G. 15

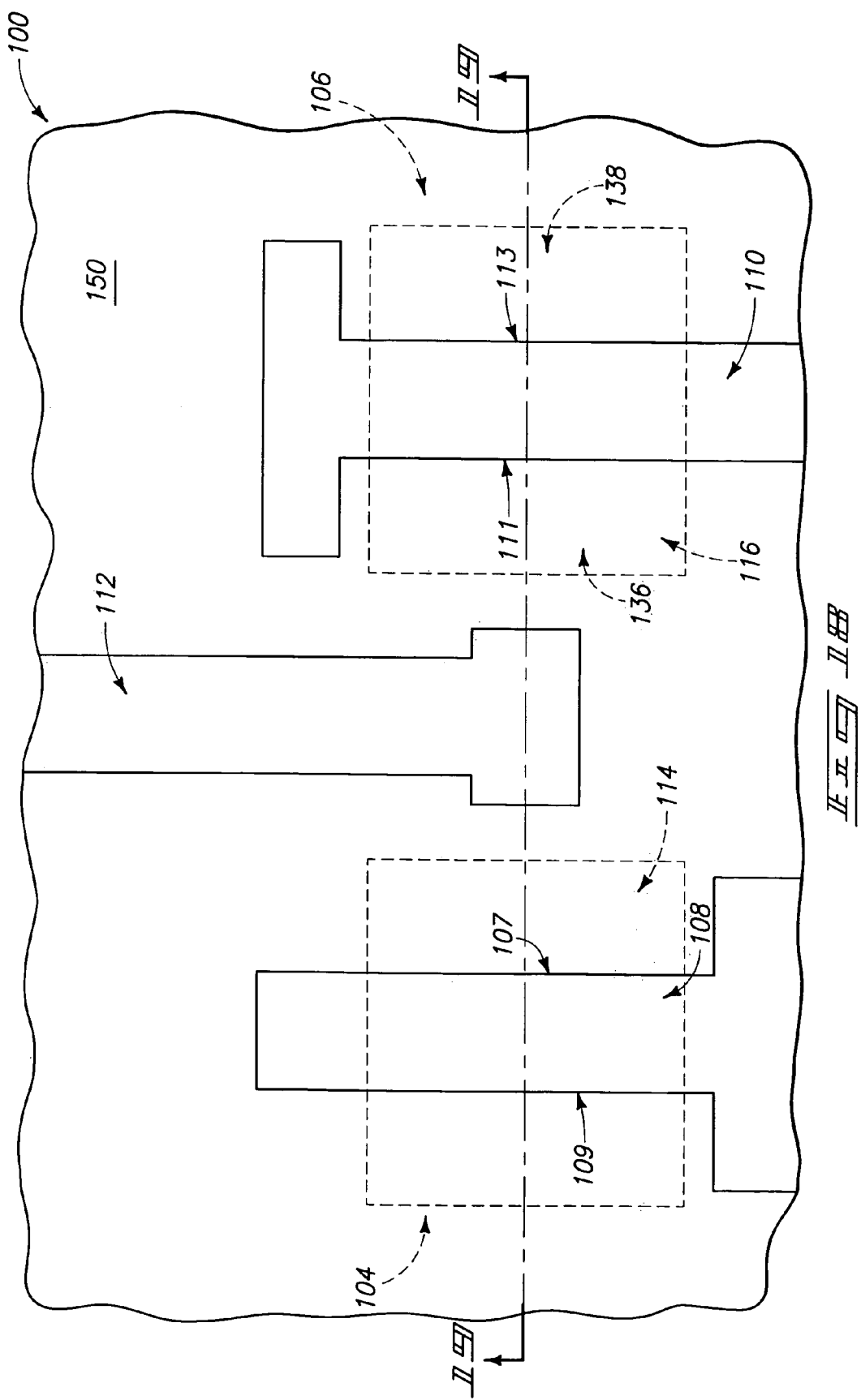

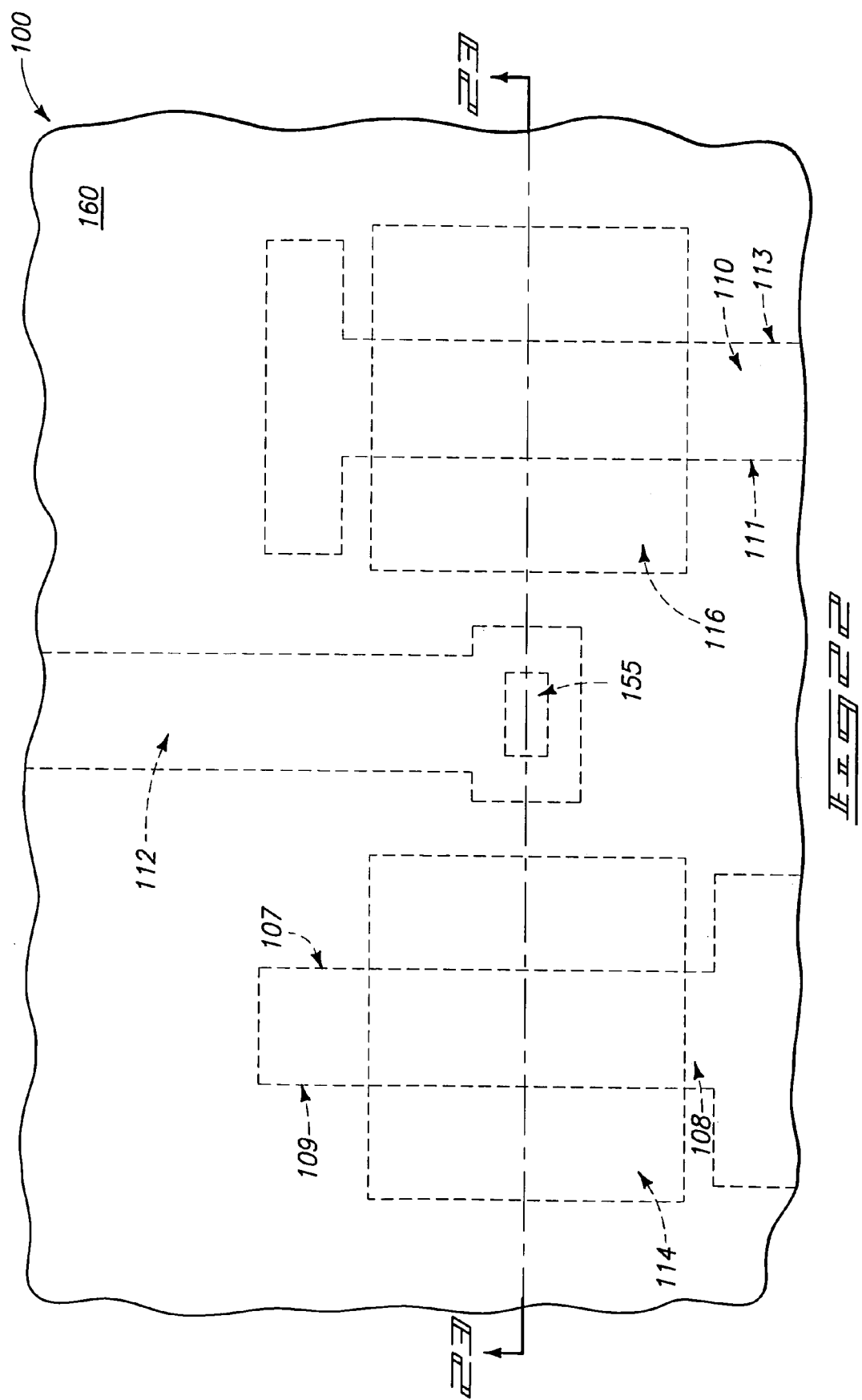

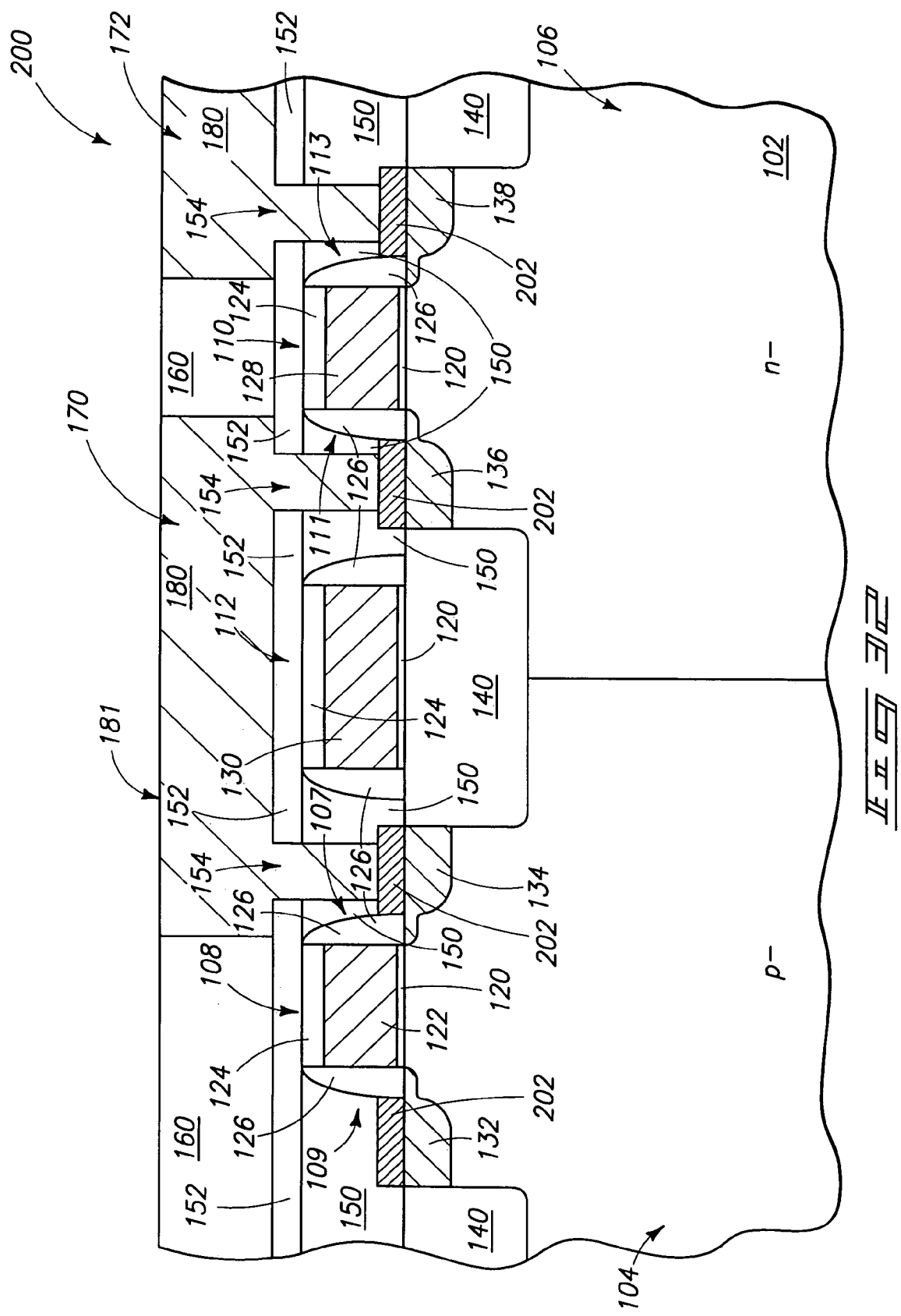

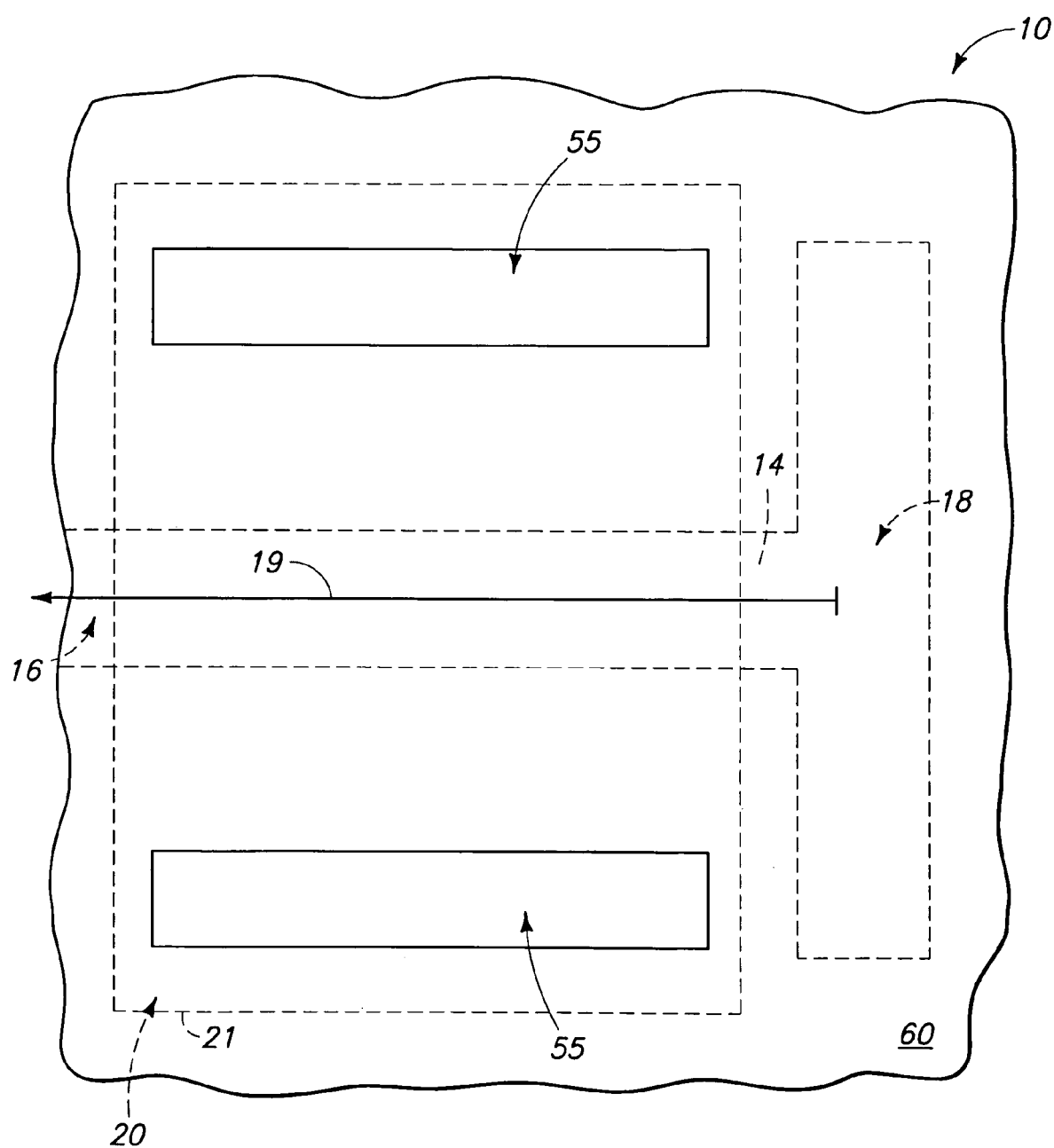
$\mathbb{F}\mathbb{I}\mathbb{G}\ 33$

METHODS OF FORMING ELECTRICAL CONNECTIONS FOR SEMICONDUCTOR CONSTRUCTIONS

TECHNICAL FIELD

The invention pertains to methods of forming electrical connections for semiconductor constructions. In particular aspects, the invention pertains to methods of forming electrical connections to source/drain regions, and to methods of forming complementary metal oxide semiconductor constructions.

BACKGROUND OF THE INVENTION

Electrical interconnections are utilized for numerous semiconductor devices and assemblies. The interconnections can be utilized in, for example, electrically connecting source/drain regions of either p-type metal-oxide-semiconductor (PMOS) field effect transistors or n-type metal-oxide-semiconductor (NMOS) field effect transistors. The electrical connections can also be utilized for coupling PMOS transistor devices with NMOS transistor devices in complementary metal-oxide-semiconductor (CMOS) structures. Exemplary devices which can utilize CMOS structures are CMOS inverters and various static random access memory (SRAM) constructions.

Continuing goals of semiconductor device processing are to increase the scale of integration, simplify processing, and reduce costs. It is desired to create new methods of forming electrical interconnections which progress toward one or more of such continuing goals.

Inventive aspects described herein can be particular useful for forming electrical interconnections to source/drain regions associated with field effect transistors. However, it is to be understood that although the invention is primarily described herein relative to such application, the invention can also be utilized in other semiconductor fabrication applications, as will be recognized by persons of ordinary skill in the art.

SUMMARY OF THE INVENTION

In one aspect, the invention includes a method of forming an electrical connection for a semiconductor construction. A semiconductor substrate is provided. The substrate has a conductive line thereover, and has at least one diffusion region therein and adjacent the conductive line. The line extends along a first axis. A patterned etch stop is formed over the at least one diffusion region. The patterned etch stop has a plurality of openings extending therethrough. At least some of the openings are along a row extending along an axis substantially parallel to the first axis, and directly over the diffusion region. An electrically insulative material is formed over the patterned etch stop. The electrically insulative material is exposed to an etch which forms a trench extending through the electrically insulative material to the patterned etch stop, and the etch also extends two or more of the openings toward the diffusion region. At least a portion of the trench is directly over the openings. An electrically conductive material is formed within the openings and within the trench. The electrically conductive material is in electrical connection with the diffusion region.

In one aspect, the invention encompasses a method of forming an electrical connection to a plurality of source/drain regions. A semiconductor substrate is provided, and a transistor gate line is provided over the substrate. The transistor gate line has a pair of opposing sides. A plurality of source/drain diffusion regions are provided within the substrate and along at least one of the sides of the transistor gate line. A first electrically insulative material is formed over the source/drain diffusion regions. A patterned etch stop is formed over the first electrically insulative material. The patterned etch stop has a plurality of openings extending therethrough, with at least some of the openings being directly over at least some of the source/drain diffusion regions. A second electrically insulative material is formed over the patterned etch stop. The first and second electrically insulative materials are etched to form a trench extending through the second electrically insulative material to the patterned etch stop and to extend some of the openings within the patterned etch stop into the first electrically insulative material. At least a portion of the trench is directly over the openings. An electrically conductive material is formed within the openings and within the trench. The electrically conductive material is in electrical connection with the source/drain diffusion regions.

In one aspect, the invention encompasses a method of forming a CMOS construction. A semiconductor substrate is provided. The substrate has a semiconductor base with a NMOS region and a PMOS region definied therein, a first conductive line over the NMOS region and a second conductive line over the PMOS region, a plurality of NMOS source/drain diffusion regions within the base and along a side of the first conductive line, and a plurality of PMOS source/drain diffusion regions within the base and along the side of the second conductive line. A patterned etch stop is formed over the NMOS and PMOS source/drain regions. The patterned etch stop has a plurality of openings extending therethrough. A first set of the openings is in one-to-one correspondence with the NMOS source/drain diffusion regions and a second set of the openings is in one-to-one correspondence with the PMOS source/drain diffusion regions. An electrically insulative material is formed over the patterned etch stop. An etch is utilized to form a trench extending through the electrically insulative material to the patterned etch stop and to extend the first and second sets of openings to at least proximate the NMOS source/drain diffusion regions and the PMOS source/drain diffusion regions, respectively. The trench has a first portion directly over the first set of openings and second portion directly over the second set of openings. An electrically conductive material is formed within the first and second sets of openings and within the trench. The electrically conductive material is in electrical connection with the PMOS and NMOS source/drain diffusion regions.

BRIEF DESCRIPTION OF THE DRAWINGS

Preferred embodiments of the invention are described below with reference to the following accompanying drawings.

FIGS. 1–3 are diagrammatic views of a semiconductor wafer fragment at a preliminary processing stage of an exemplary aspect of the present invention. FIG. 1 is a diagrammatic top view, and FIGS. 2 and 3 are diagrammatic cross-sectional views along the lines 2—2 and 3—3 of FIG. 1, respectively. Additionally, the cross-section of FIG. 2 is shown along the line 2—2 of FIG. 3 and the cross-section of FIG. 2 is shown along the line 2—2 of FIG. 3.

FIGS. 4–6 are views of the fragments of FIGS. 1–3, respectively, shown at a processing stage subsequent to that of FIGS. 1–3. The views of FIGS. 5 and 6 are shown along the lines 5—5 and 6—6 of FIG. 4, respectively. Also, the cross-section of FIG. 6 is along the line 6—6 of FIG. 5 and the cross-section of FIG. 5 is along the line 5—5 of FIG. 6.

FIGS. 7–9 are views of the fragments of FIGS. 1–3, respectively, shown at a processing stage subsequent to that of FIGS. 4–6. The cross-sections of FIGS. 8 and 9 are along the lines 8—8 and 9—9, respectively, of FIG. 7. Also, the cross-section of FIG. 9 is along the line 9—9 of FIG. 8 and the cross-section of FIG. 8 is along the line 8—8 of FIG. 9.

FIGS. 10–12 are views of the fragments of FIGS. 1–3, respectively, shown at a processing stage subsequent to that of FIGS. 7–9. The cross-sections of FIGS. 11 and 12 are along the lines 11—11 and 12—12 of FIG. 10. Also, the cross-section of FIG. 12 is along the line 12—12 of FIG. 11 and the cross-section of FIG. 11 is along the line 11—11 of FIG. 12.

FIGS. 13–15 are views of the fragments of FIGS. 1–3, respectively, shown at a processing stage subsequent to that of FIGS. 10–12. The cross-sections of FIGS. 14 and 15 are along the lines 14—14 and 15—15 of FIG. 13. Also, the cross-section of FIG. 15 is along the line 15—15 of FIG. 14 and the cross-section of FIG. 14 is along the line 14—14 of FIG. 15.

FIGS. 16 and 17 are fragmentary views of a semiconductor wafer fragment at a preliminary processing stage in accordance with a second aspect of the present invention. FIG. 16 is a top view, and FIG. 17 is a cross-sectional view along the line 17—17 of FIG. 16.

FIGS. 18 and 19 are views of the fragments of FIGS. 16 and 17, respectively, shown at a processing stage subsequent to that of FIGS. 16 and 17. The cross-section of FIG. 19 is along the line 19—19 of FIG. 18.

FIGS. 20 and 21 are views of the fragments of FIGS. 16 and 17, respectively, shown at a processing stage subsequent to that of FIGS. 18 and 19. The cross-section of FIG. 21 is along the line 21—21 of FIG. 20.

FIGS. 22 and 23 are views of the fragments of FIGS. 16 and 17, respectively, shown at a processing stage subsequent to that of FIGS. 20 and 21. The cross-section of FIG. 23 is along the line 23—23 of FIG. 22.

FIG. 32 is a cross-sectional view of the FIG. 16 wafer fragment shown at a processing stage subsequent to that of FIG. 19 in accordance with an aspect of the invention alternative to that described with reference to FIGS. 20–30.

FIG. 33 is a top view of a semiconductor wafer fragment at a processing stage analogous to the that of FIG. 4 in accordance with an aspect of the invention alternative to that of FIG. 4.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The invention includes methods by which active regions can be strapped (i.e., conductively interconnected) utilizing trench etches. The active regions can be along the same conductive line as one another, or along different conductive lines. An aspect of the invention in which active regions along a common conductive line are strapped to one another is described with reference to FIGS. 1–15, and aspects in which active regions associated with different conductive lines are strapped to one another are described with reference to FIGS. 16–30, and 32.

Figure 1:
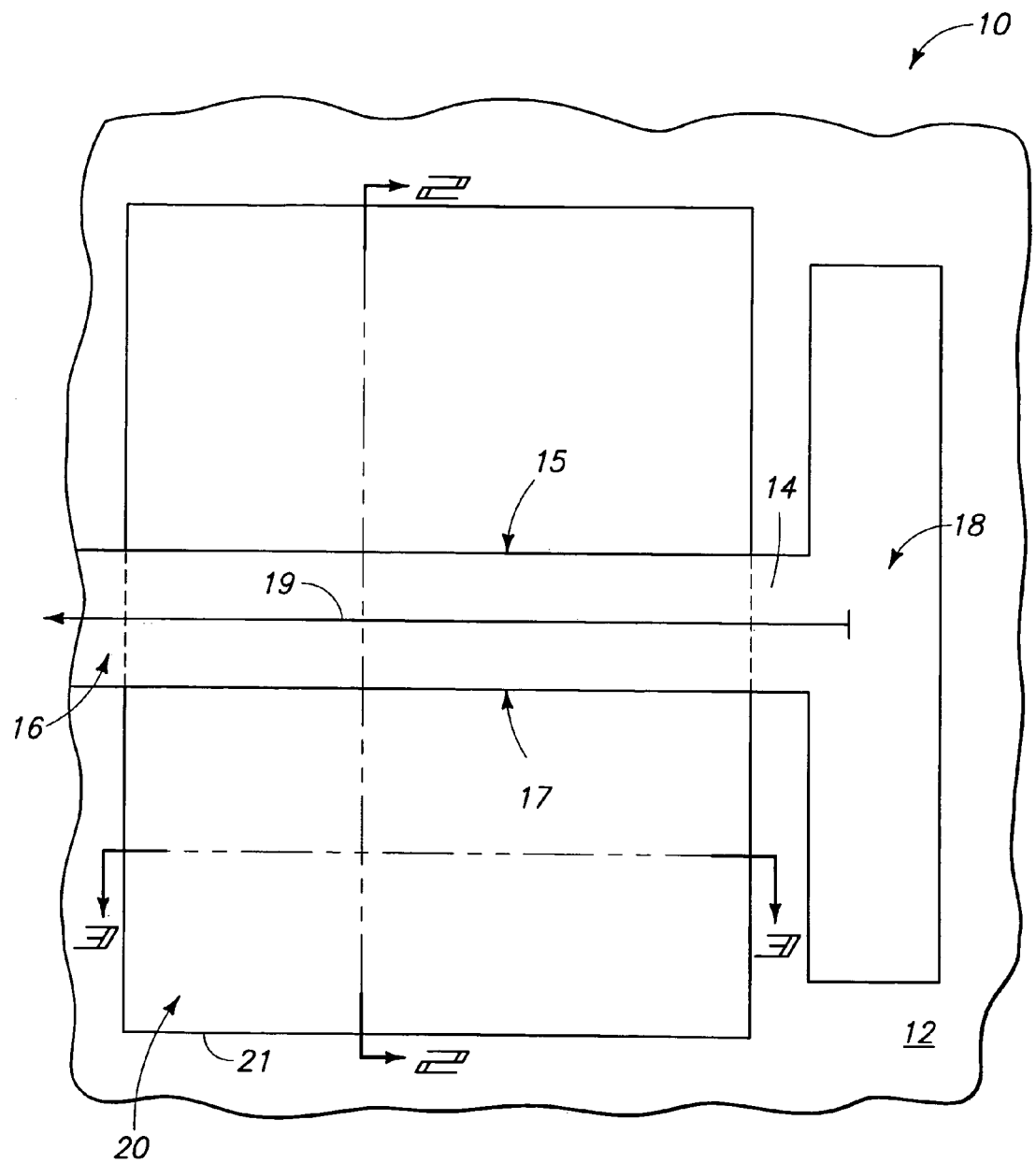
Figure 2H:
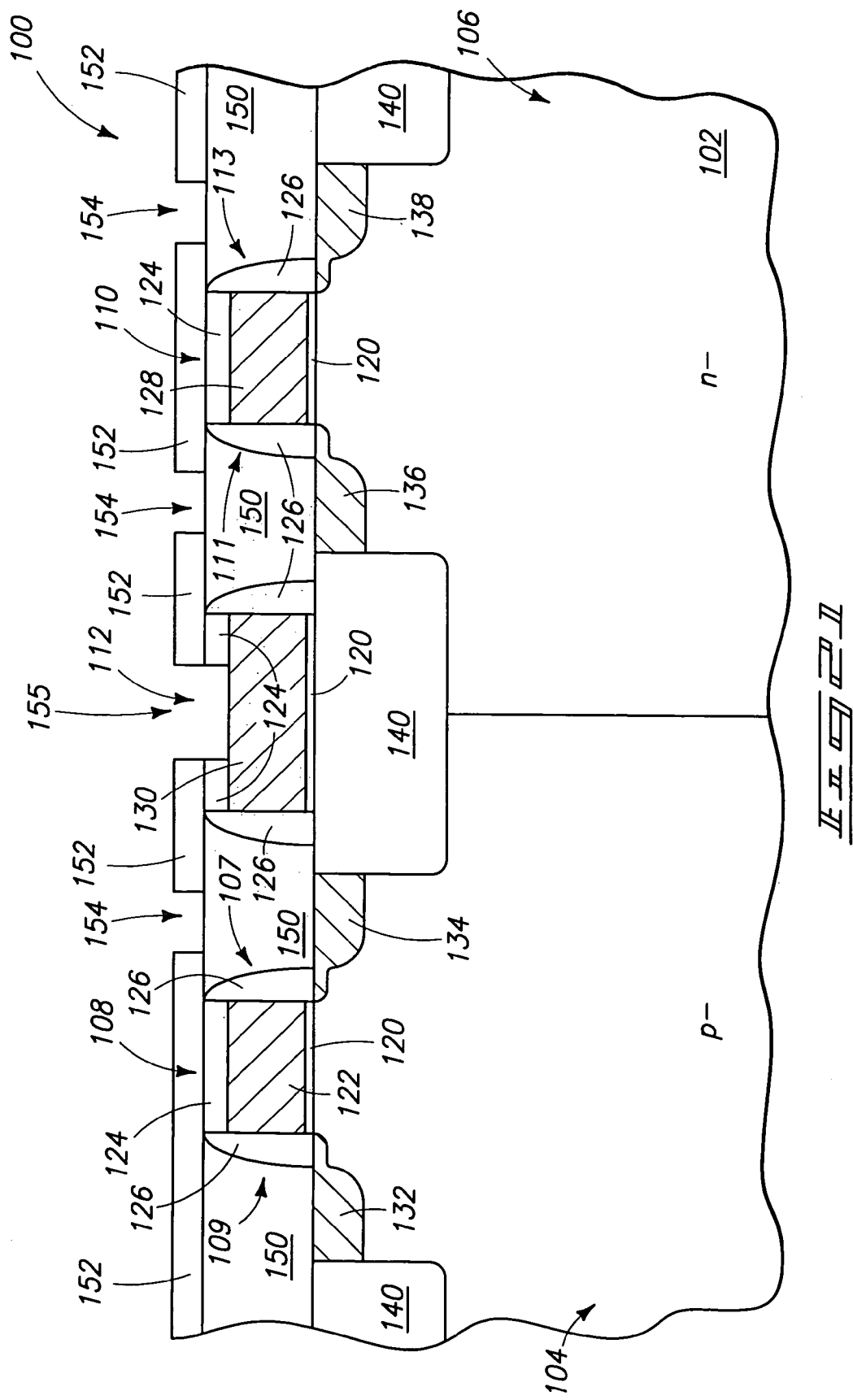

Referring initially to FIGS. 1–3, a semiconductor wafer fragment 10 is illustrated at a preliminary processing stage of the exemplary first aspect of the present invention. Wafer fragment 10 is shown in FIG. 1 to comprise a semiconductor base 12 having a conductive line 14 thereover. Conductive line 14 has a horizontally extending linear segment 16 which is shown to terminate in a tee 18. The linear segment 16 extends along an axis 19. Axis 19 can be referred to as a first axis in the discussion that follows to distinguish the axis 19 from other axes that are discussed below.

An active region 20 extends around the linear segment 16 of line 14. A boundary of active region 20 is demarcated with a line 21. In the shown aspect of the invention, active region 20 has a rectangular or box-like shape. The active region extends adjacent line 14, and also within the base 12 underlying line 14.

FIGS. 2 and 3 illustrate cross-sections along the line 2—2 and 3—3, respectively, of FIG. 1. FIG. 2 shows that line 14 comprises a lower electrically insulative region 22, a middle electrically conductive region 24, and an upper electrically insulative region 26.

Electrically insulative region 22 can comprise any suitable electrically insulative material, and in particular aspects will comprise, consist essentially of, or consist of silicon dioxide, nitrided oxide or high-k dielectric materials.

Conductive region 24 can comprise any suitable electrically conductive material, and in particular aspects will comprise, consist essentially of, or consist of one or more of metals (such as, for example, tungsten), metal compounds (such as, for example, tungsten nitride and/or titanium nitride), and conductively-doped semiconductor materials (such as, for example, conductively-doped polycrystalline silicon and/or conductively-doped amorphous silicon). In particular aspects, conductive material 24 can consist of a lower portion consisting of conductively-doped polycrystalline silicon and an upper portion consisting of tungsten, or conductive silicide, such as, for example, one or more of tungsten silicide, cobalt silicide, nickel silicide, titanium silicide and tantalum silicide.

Upper insulative region 26 can comprise any suitable material, and in particular aspects will comprise, consist essentially of, or consist of one or both of silicon nitride and silicon dioxide.

Line 14 is referred to as a conductive line, even though, as shown, the line can comprise insulative materials in addition to conductive materials.

Line 14 has a pair of opposing lateral sidewalls 15 and 17. Spacers 28 are formed along the opposing sidewalls. Spacers 28 can comprise anisotropically-etched electrically insulative materials. The electrically insulative materials can comprise any suitable materials, including, for example, materials comprising, consisting essentially of, or consisting of one or both of silicon nitride and silicon dioxide. The insulative spacers 28 are not shown in the diagram of FIG. 1 in order to simplify the diagram.

FIG. 2 shows conductively-doped diffusion regions 30 and 32 extending into semiconductor base 12. Regions 30 and 32 can comprise either n-type doped or p-type doped regions, as will be understood by persons of ordinary skill in the art. Diffusion regions 30 and 32 are adjacent conductive line 14, and are on opposing sides of the conductive line relative to one another. A channel region 35 extends beneath line 14 and between source/drain regions 30 and 32. The source/drain regions and channel region are together comprised by the active region 20. Conductive line 14 can be considered to comprise a field effect transistor gate in the cross-section of FIG. 2, with such gate configured to turn on or off the channel, thus interconnecting or disconnecting source/drain regions 30 and 32.

FIG. 3 shows that diffusion region 32 can be one of several diffusion regions formed along the conductive line 14. Specifically, FIG. 3 shows a plurality of isolation regions 34 extending into base 12, and further shows a plurality of diffusion regions 40, 42 and 44, in addition to region 32, with the regions 40, 42, 32 and 44 being electrically isolated from one another by the isolation regions 34. Isolation regions 34 can comprise any suitable structure, including, for example, shallow trench isolation structures. If isolation structures 34 comprise shallow trench isolation structures, the structures can comprise, consist essentially of, or consist of, for example, silicon dioxide.

The diffusion regions 40, 42, 32 and 44 extend along the axis 19, as can be seen in comparing FIGS. 1 and 3. It is noted that the conductive line 14 would be visible in the view of FIG. 3 as being behind the plane of the cross-section of FIG. 3. However, conductive line 14 is not shown in FIG. 3 in order to simplify the drawing, and in order to emphasize that the cross-section of FIG. 3 is along a different plane than the plane of line 14.

The diffusion regions 40, 42, 32 and 44 can each be considered a separate source/drain region associated with a transistor device comprised by line 14, with the view of FIG. 2 showing an exemplary transistor device comprising the source/drain region 32.

The diffusion regions 40, 42, 32 and 44 can be formed by implanting suitable conductivity-enhancing dopant into a semiconductor material of base 12. The base 12 can comprise any suitable semiconductor material, including, for example, monocrystalline silicon lightly-background doped with an appropriate dopant (p-type or n-type dopant). Base 12 can be referred to as a semiconductor substrate in the discussion and claims of this disclosure, but it is to be understood that the term "substrate" is broad enough to encompass other structures in addition to, or alternatively to, base 12. To aid in interpretation of the claims that follow, the terms "semiconductive substrate" and "semiconductor substrate" are defined to mean any construction comprising semiconductive material, including, but not limited to, bulk semiconductive materials such as a semiconductive wafer (either alone or in assemblies comprising other materials thereon), and semiconductive material layers (either alone or in assemblies comprising other materials). The term "substrate" refers to any supporting structure, including, but not limited to, the semiconductive substrates described above.

Figure 5:
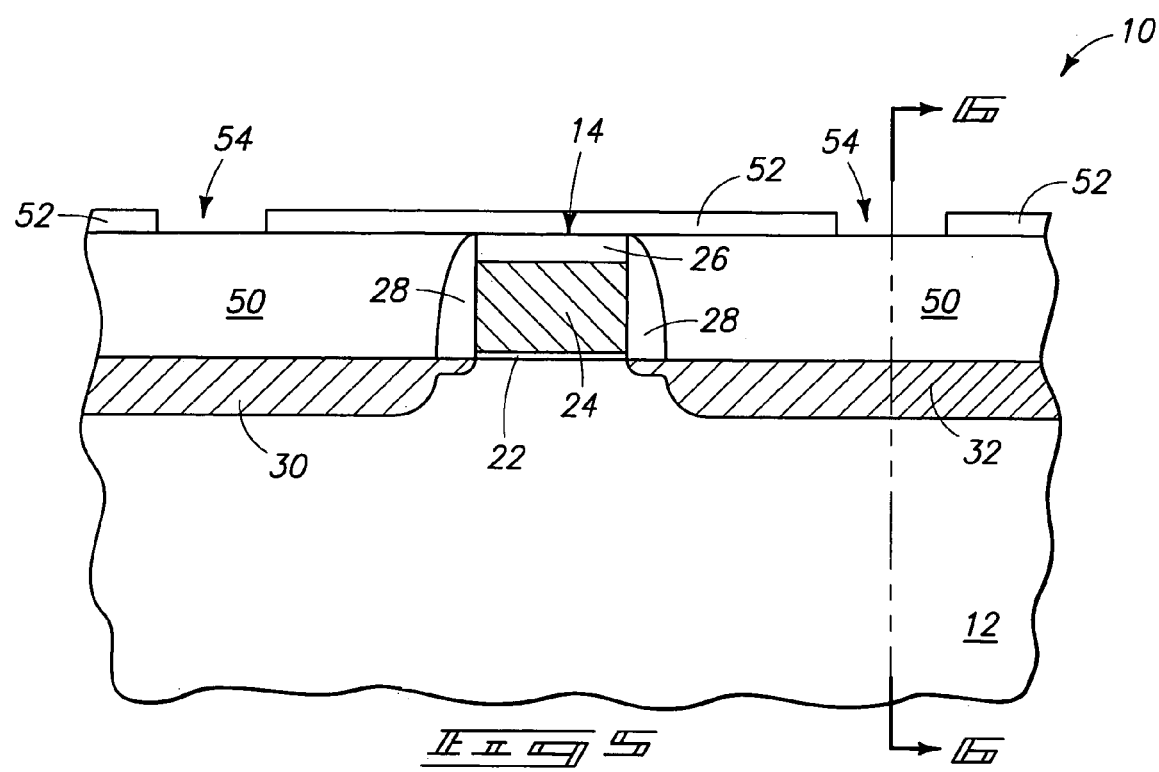
Figure 6:
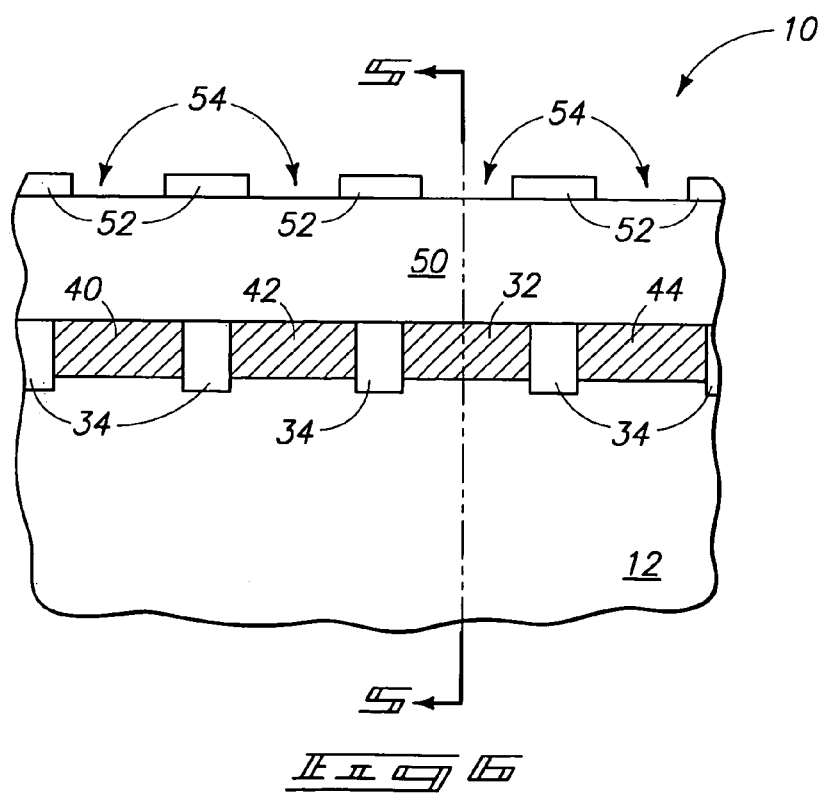

Referring to FIGS. 4–6, an electrically insulative material 50 is formed over base 12, and specifically over diffusion regions 30, 32, 40, 42 and 44. Insulative material 50 can comprise any suitable material, and in particular aspects will comprise doped or undoped silicon oxide, with example materials being borophosphosilicate glass (BPSG) and spin-on-dielectric (SOD). Accordingly, insulative material 50 can, in particular aspects, comprise, consist essentially of, or consist of BPSG and/or SOD.

A patterned layer 52 is formed over insulative material 50. Patterned layer 52 will typically comprise a material to which insulative material 50 can be selectively etched. In other words, material 52 will comprise a material which etches more slowly under particular conditions than does material 50. In exemplary aspects of the invention, material 52 can comprise, consist essentially of, or consist of one or more of aluminum, silicon, oxygen and nitrogen. For instance, material 52 can comprise, consist essentially of, or consist of one or more of aluminum oxide, silicon dioxide, silicon nitride and silicon oxynitride. In such aspects, material 50 can consist of a doped oxide, such as, for example, BPSG to be selectively etchable relative to material 52. Specifically, etch conditions are known to persons of ordinary skill in the art which selectively etch a doped silicon oxide relative to aluminum oxide, silicon nitride, silicon oxynitride, and/or undoped silicon dioxide. The term "undoped" is utilized to distinguish a silicon dioxide material lacking boron and/or phosphorous and/or other impurities from a doped silicon oxide (such as BPSG). The undoped oxide may be entirely undoped (i.e. may contain no measurable dopant), or may simply be less doped than a doped silicon oxide so that the etch rate of the doped silicon oxide is faster than the etch rate of the undoped silicon dioxide.

Layer 52 is shown having a substantially planar upper surface. The shown structure can be formed as follows. Initially, insulative material 50 is formed over the base 12. An upper surface of the material 50 is then planarized (using, for example, chemical-mechanical polishing). Subsequently, layer 52 is formed to be conformal over the planarized upper surface of material 50.

Patterned layer 52 has openings 54 extending therethrough, with such openings being directly over diffusion regions that are along the line 14 (such as, for example, the diffusion regions 30, 32, 40, 42 and 44). Layer 52 can be formed into the shown pattern utilizing any suitable method. An exemplary method is photolithographic processing. Specifically, an unpatterned layer 52 can be initially formed over layer 50, and subsequently the shown pattern of openings can be formed within layer 52 by photolithographically forming a photoresist mask over layer 52 to define the location of the openings, etching the openings into the desired locations with a suitable etch of layer 52, and then removing the photoresist mask.

The openings 54 are shown to be formed along both sides of the horizontally extending linear segment 16 of line 14. Specifically, four openings are shown on each of the opposing sides of the line. The four openings along a side of the line are along a row, with such row extending along an axis substantially parallel to the axis 19 of the linear segment 16 of line 14. The term "substantially parallel" is utilized to indicate that the two axes referred to are parallel to one another within the processing and measurement tolerances of a particular process, which includes, but is not limited to, aspects in which the axes are exactly parallel to one another. Although a plurality of four openings are shown formed on opposing sides of the line, it is to be understood that each set of openings could be replaced with a single long opening (i.e., a slot or trench). Thus, the two four-opening sets on the opposing sides of the line could be replaced with a pair of elongated slots that are on opposing sides of the line. Such aspect of the invention is shown in FIG. 33, with the elongated slots being labeled 55.

FIG. 4 shows the material 52 covering an entirety of the top surface of fragment 10, except for the windows 54. The conductive line 14 and active region 20 are shown in phantom view in FIG. 4 to indicate that such structures are buried beneath layer 52.

Figure 7:
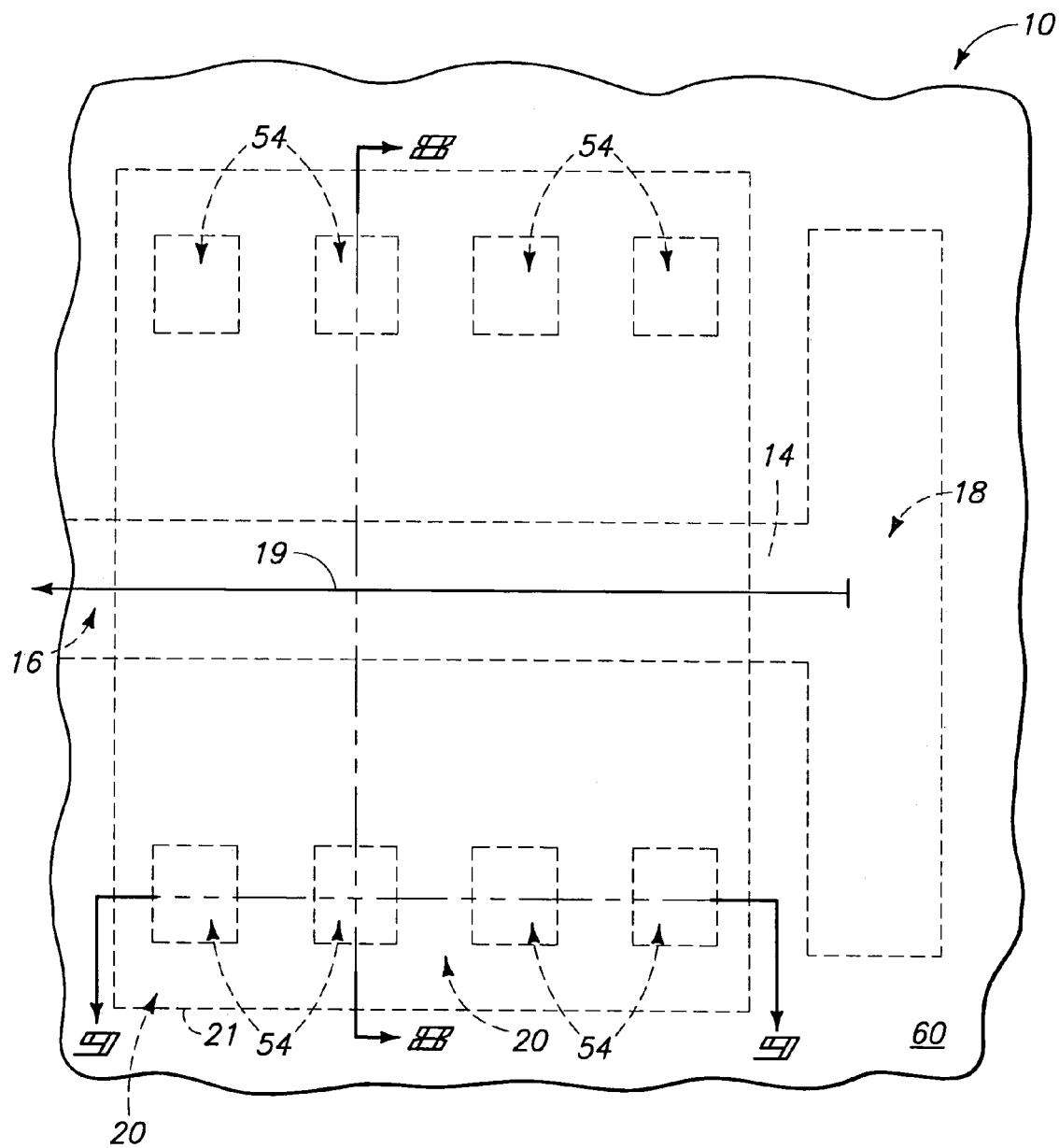

Referring next to FIGS. 7–9, an insulative material 60 is formed over patterned layer 52 and insulative material 50. Insulative materials 50 and 60 can be referred to as a first electrically insulative material and a second electrically insulative material, respectively, to distinguish the materials from one another. The first and second electrically insulative materials 50 and 60 can comprise differing compositions from one another, or the same composition as one another. In particular aspects, insulative materials 50 and 60 both comprise doped silicon oxide. In some aspects, insulative materials 50 and 60 can both consist essentially of, or consist of the same doped silicon oxide, such as, for example, BPSG.

Figure 11:
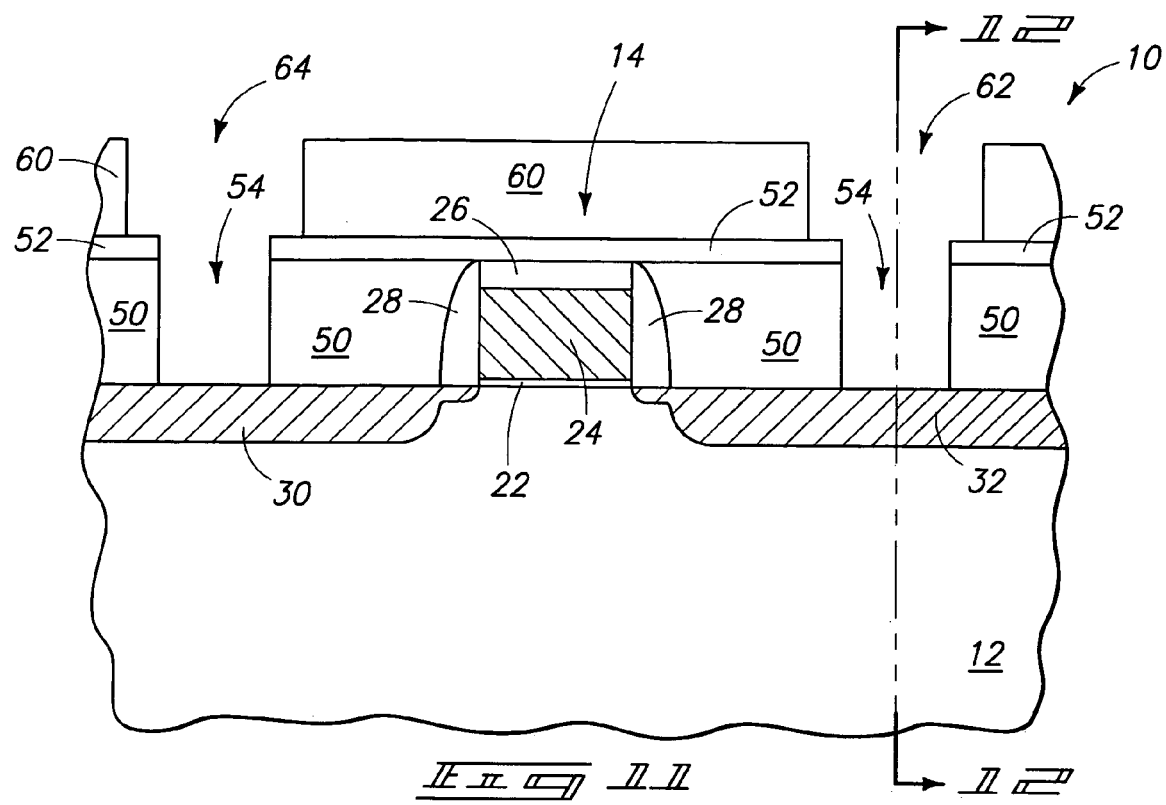
Figure 12:
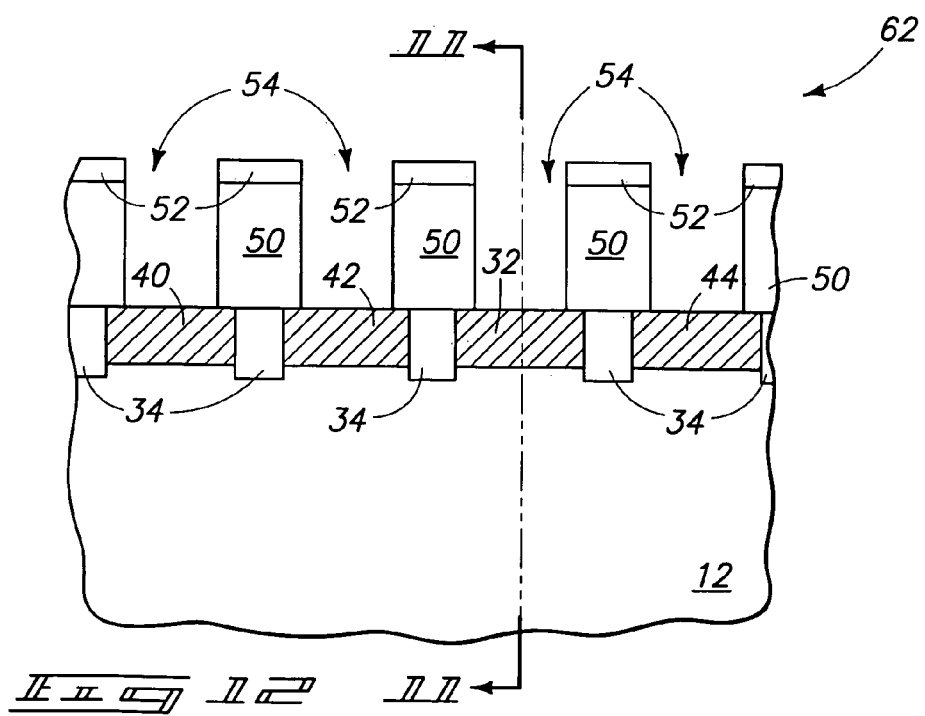

Referring to FIGS. 10–12, an etch is utilized to form trenches 62 and 64 within insulative material 60. The etch also extends openings 54 to an upper surface of base 12, and accordingly to diffusion regions 30, 32, 40, 42 and 44. The shown trenches 62 and 64 have portions directly over openings 54, and such portions extend along axes which are substantially parallel to the axis 19 of conductive line 14. The trenches may have other portions (not shown in FIG. 10) which extend in other orientations besides substantially parallel to axis 19. Regardless, in typical aspects of the invention, at least some portions of the trenches are linear and extend along axes substantially parallel to the axis 19 of conductive line 14. The axes along which trenches 62 and 64 extend can be referred to as a second axis and a third axis, respectively, to distinguish such axes from the first axis along which conductive line 14 extends.

Although peripheries of trenches 62 and 64 are shown extending entirely around openings 54, it is to be understood that the invention encompasses other aspects in which the openings 54 are not enclosed by the peripheries of trenches 62 and 64.

The etch utilized to form trenches 62 and 64 is selective for material 60 relative to material 52. In other words, the etch removes material 60 faster than it removes material 52. The etch can be, in some aspects, highly selective for material 60 relative to material 52 so that material 52 is not substantially removed by the etch even though a large portion of material 60 is removed.

In applications in which materials 60 and 50 are the same compositions as one another, the same etch conditions can be utilized for forming trenches 62 and 64 as are utilized for extending openings 54 through material 50. If materials 60 and 50 are different from one another, the etch utilized to form trenches 62 and 64, and subsequently to extend openings 54, can comprise a change in etching conditions between the formation of trenches (62 and 64) and the extension of the openings (54) into material 50.

Material 52 can be referred to as a "etch stop" in some aspects of the invention to indicate that the etch through insulative material 60 substantially stops at layer 52. In other words, the term "etch stop" indicates that the etch of insulative material 60 is selective for material 60 relative to material 52. The term "etch stop" includes, but is not limited to, applications in which etch for material 60 entirely stops at material 52 (i.e., applications in which the etch for material 60 is 100% selective relative to material 52). Accordingly, the term "etch stop" is to be understood to encompass any applications in which removal of material 60 relative to material 52 is selective for material 60, including, but not limited to, applications in which the etch rate of material 52 is much lower than the etch rate of material 60.

Although openings 54 are shown being extended to an upper surface of base 12, it is to be understood that the openings may, in other aspects, be extended toward an upper surface of base 12 but not entirely to such upper surface. Instead, the openings may be extended to proximate the diffusion regions 30, 32, 40, 42 and 44 within base 12, without extending entirely to such diffusion regions. The openings can be referred to as being extended to "at least proximate" the diffusion regions to indicate that the openings may be extended entirely to the diffusion regions, or only to proximate the diffusion regions. In some aspects of the invention, conductive structures (for example, conductive pedestals; not shown in FIGS. 1–12) are over the diffusion regions. Openings 54 can then be extended to the conductive structures, or at least close enough to the conductive structures so that electrical connection can be subsequently formed to the conductive structure by an appropriate material formed within the openings.

The insulative material 60 is not shown in FIG. 12, even though the material would be visible behind the plane of the cross-section of FIG. 12. The material 60 is not shown in order to simplify the drawing, and in order to emphasize that the material 60 is not present along the plane of the cross-section of FIG. 12.

Figure 13:
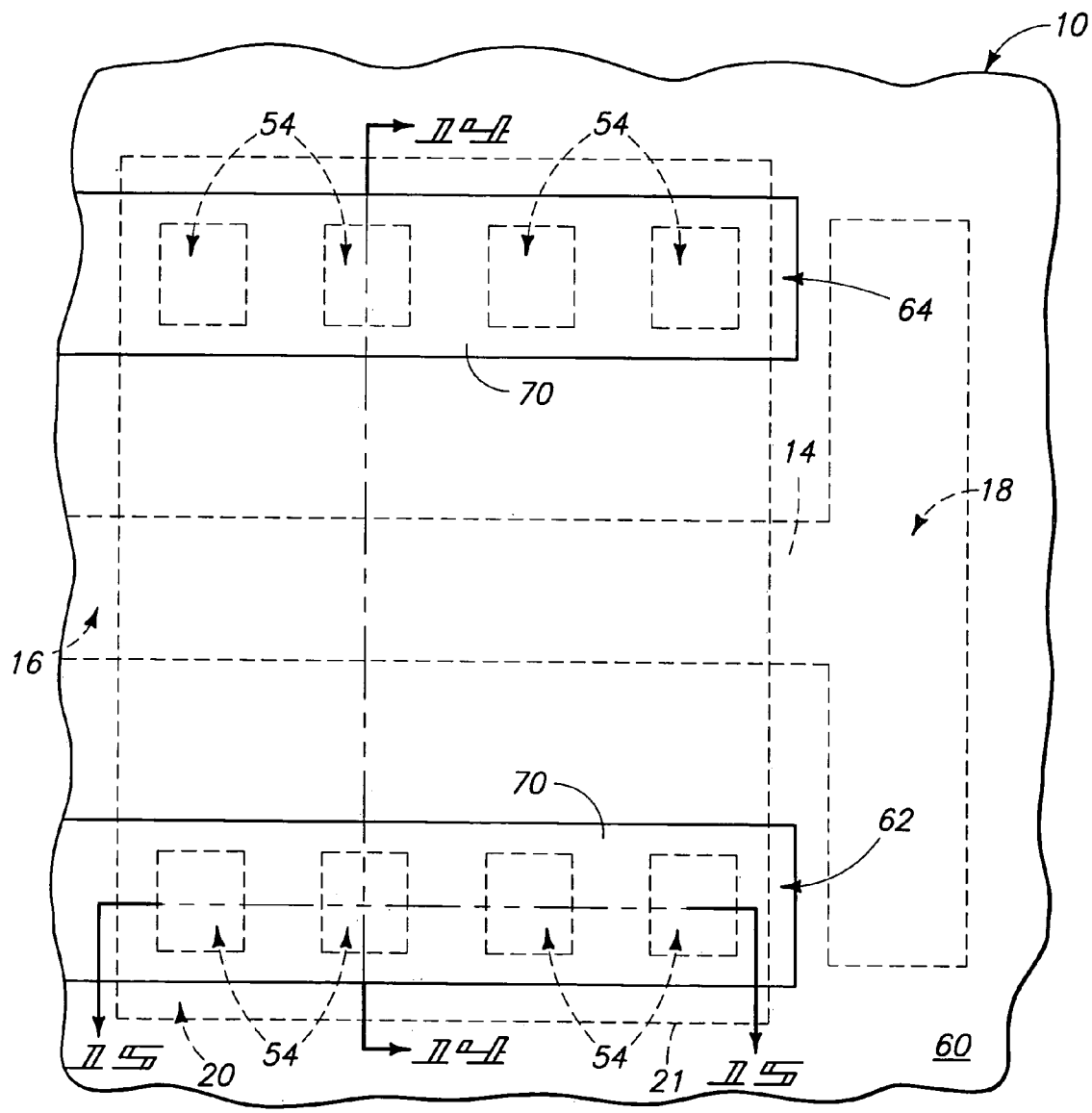

Referring next to FIGS. 13–15, a conductive material 70 is formed within trenches 62 and 64, and within openings 54. The conductive material 70 electrically connects with the diffusion regions 30, 32, 40, 42 and 44. Electrically conductive material 70 can comprise any suitable material, including, for example, metal, metal compounds, and/or conductively-doped semiconductor materials, such as, for example, conductively-doped silicon. In particular aspects, conductive material 70 will comprise a thin layer of metal nitride (such as, for example, titanium nitride or tungsten nitride), and a thick layer of tungsten. The thin layer of metal nitride is utilized to adhere the thick layer within trenches 62 and 64, and within openings 54.

In the shown aspect of the invention, the conductive material within trench 62 is electrically isolated from the material within trench 64, and the conductive material 70 comprises a common planarized upper surface 74 with insulative material 60. The shown construction can be formed by, for example, depositing the conductive material 70 within the trenches and openings and over an upper surface of insulative material 60, and subsequently planarizing the conductive material either alone, or in combination with material 60, to remove the conductive material from over an uppermost remaining surface of material 60 and form the planarized upper surface 74. The planarization can be accomplished utilizing, for example, chemical-mechanical polishing.

In the aspect of the invention of FIGS. 1–15, a plurality of separate diffusion regions are formed along the opposing sides of conductive line 14. The separate diffusion regions can correspond to source/drain diffusion regions associated with separate transistor devices. Accordingly, conductive line 14 can correspond to a transistor gate line, such as, for example a wordline associate with a memory array. The transistor gate line can comprise a series of transistor gates extending sequentially along a row defined by axis 19. The separate diffusion regions shown in FIGS. 3, 6, 9, 12 and 15 will be mirrored on an opposing side of conductive line 14, as indicated by FIGS. 2, 5, 8, 11 and 14. Trench 62 can be considered a first trench, and trench 64 considered a second trench which mirrors trench 62 across conductive line 14. The processing described above as occurring relative to trench 62 and the openings 54 directly beneath such trench can occur simultaneously relative to trench 64 and the openings 54 directly beneath it. The openings 54 beneath trench 62 can, in some aspects of the invention, be considered a first set of openings in a row along a first side of conductive line 14, and the openings 54 directly beneath trench 64 can be considered to be a second set of openings in a row along a second side of line 14 which is in opposing relation to the first side of line 14.

Although the openings are shown formed in a one-to-one correspondence with a plurality of diffusion regions in the processing of FIGS. 1–15, it is to be understood that the invention includes other aspects in which two or more openings are associated with a single diffusion region. For instance, the shown isolation regions 34 can be eliminated in some aspects of the invention so that diffusion regions 40, 42, 32 and 44 merge into a single, continuous diffusion region extending along a side of line 14. Another similar diffusion region can be formed along the opposing side of line 14. Each of the shown rows of openings 54 extending along the sides of the line can be formed over the single continuous diffusion regions to form multiple contacts to the single diffusion regions.

Figure 16:
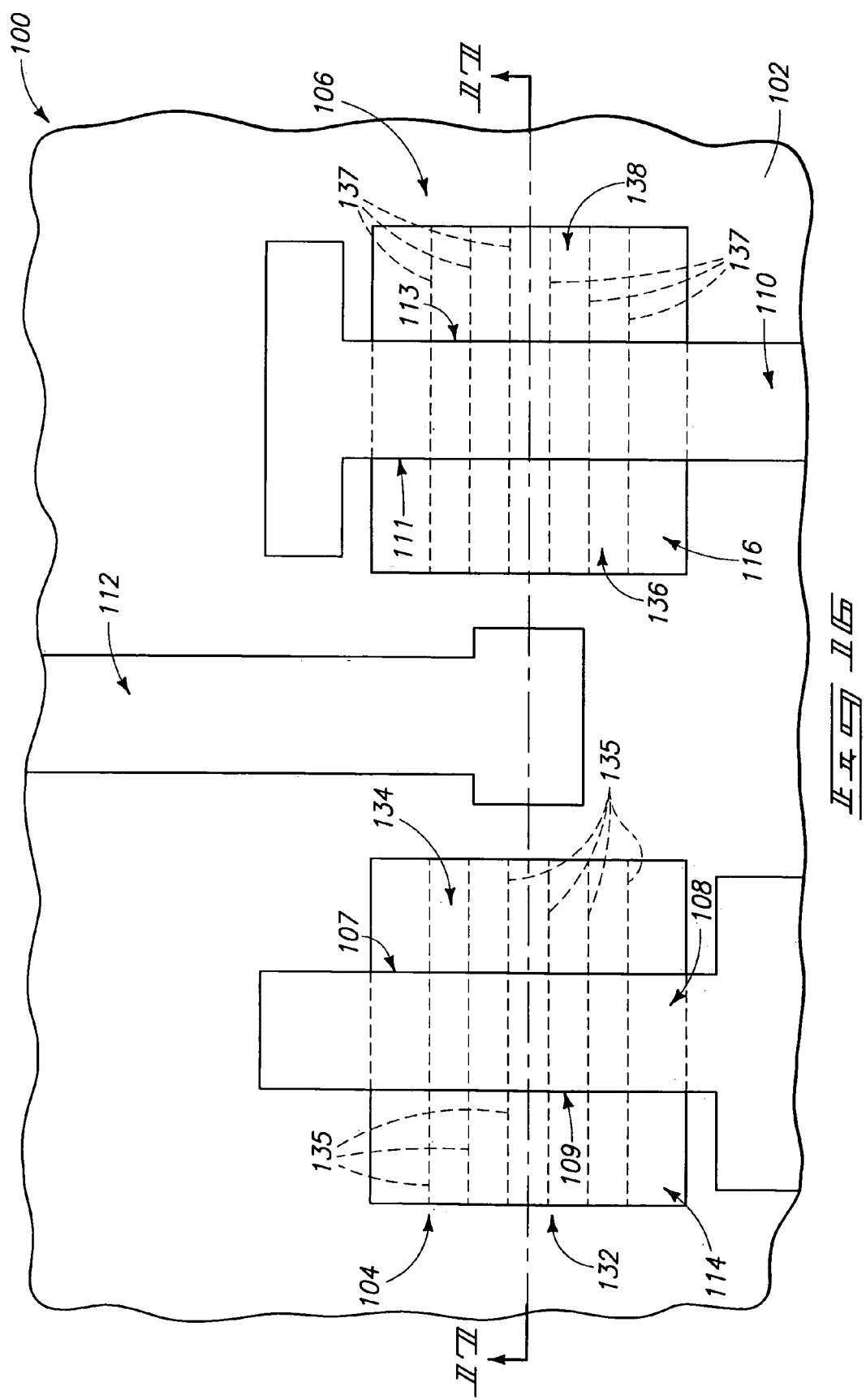
Figure 11:
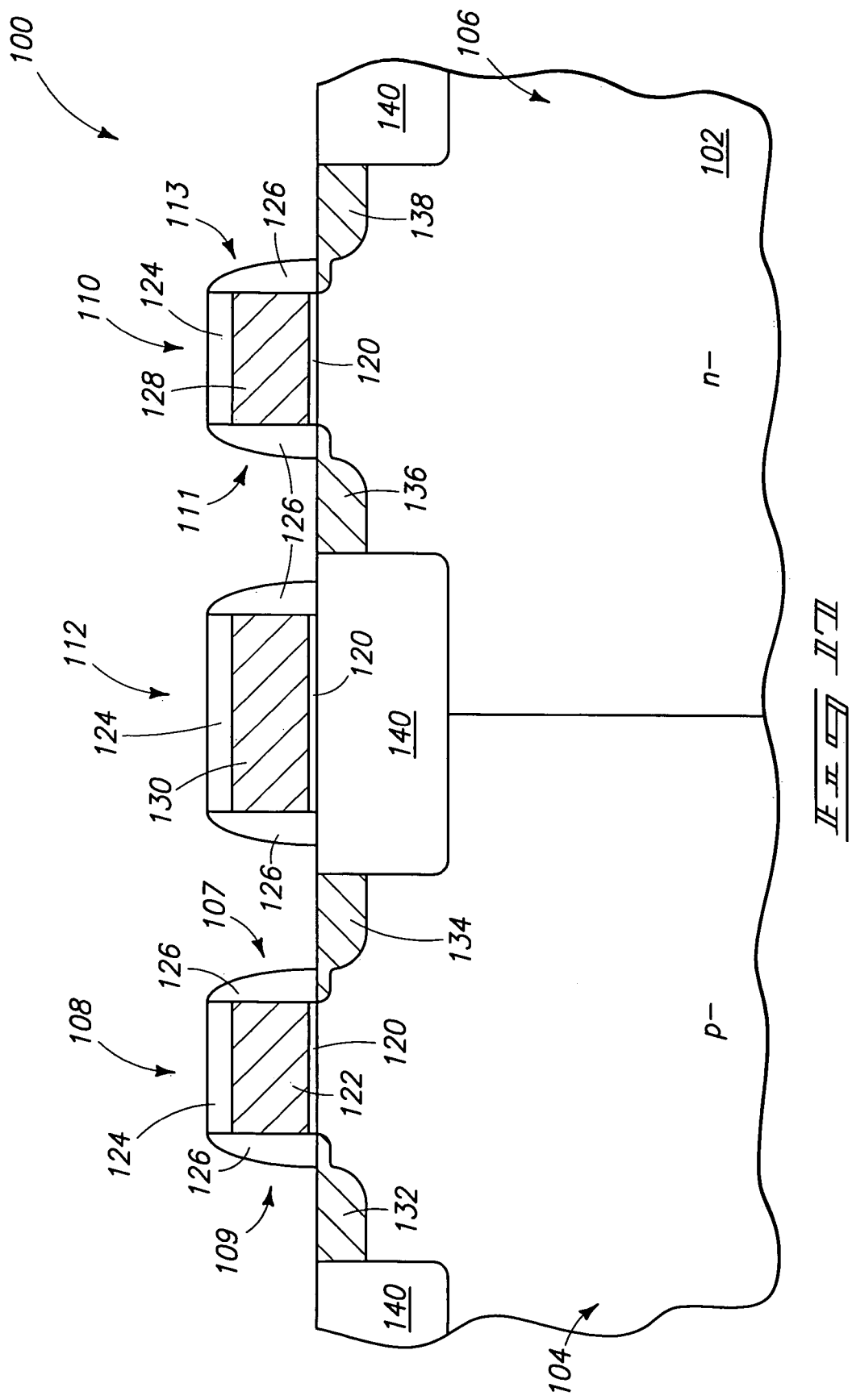

FIGS. 16–30 illustrate a second aspect of the invention. FIGS. 16 and 17 show a semiconductor wafer fragment 100 at a preliminary processing stage of the second aspect. Wafer fragment 100 comprises a substrate having a base 102. A suitable semiconductor material base is, for example, monocrystalline silicon lightly doped with background p-type dopant.

The base 102 has an NMOS region 104 and a PMOS region 106 defined therein. NMOS region 104 comprises a background p-type dopant (shown as p- in FIG. 17), and PMOS region 106 comprises a background n-type dopant (shown as n- in FIG. 17). The n-region would typically be formed as an n well in the semiconductor material base.

The fragment 100 further includes a first conductive line 108 over the NMOS region, a second conductive line 110 over the PMOS region, and a third conductive line 112 between the first and second conductive lines. The first and second conductive lines can correspond to wordlines, and accordingly can comprise a series of transistor gates. The gates will interconnect source/drain regions on opposing sides of the lines with one another.

An active region 114 is diagrammatically illustrated as a box surrounding a portion of line 108, and another active region 116 is diagrammatically illustrated as a box surrounding a portion of line 110. The active region 114 comprises a plurality of NMOS source/drain diffusion regions, and the active region 116 comprises a plurality of PMOS source/drain diffusion regions. The NMOS source/drain regions are diagrammatically illustrated by dashed lines 135 which mark separations between individual NMOS source/drain regions, and the PMOS source/drain regions are diagrammatically illustrated by dashed lines 137 which mark separations between individual PMOS source/drain regions.

Conductive line 108 comprises a pair of opposing sides 107 and 109. The NMOS source/drain diffusion regions include a first series of diffusion regions along the side 107 of line 108, and a second series of diffusion regions along the side 109 of line 108. The first and second series of diffusion regions are connected with one another through transistor gates comprised by line 108, similarly to the interconnection of separate source/drain regions discussed above with reference to FIGS. 1–15.

Conductive line 110 comprises a pair of opposing sides 111 and 113. A first series of PMOS source/drain diffusion regions is formed along side 111, and a second series of PMOS source/drain diffusion regions is formed along side 113. The first series of diffusion regions along side 111 is connected with the second series along side 113 through transistor gates comprised by line 110, similarly to the interconnections discussed above with reference to FIGS. 1–15.

Line 112 does not have source/drain regions associated therewith in the shown fragments of FIGS. 16 and 17, but rather is a conductive interconnect extending to other circuitry (not shown).

FIG. 17 shows exemplary source/drain diffusion regions along the cross-section 17—17 of FIG. 16. Specifically, NMOS source/drain diffusion regions 132 and 134 are shown along opposing sides of line 108, and PMOS source/drain diffusion regions 136 and 138 are shown along opposing sides of line 110. The NMOS source/drain regions would comprise an appropriate n-type conductivity-enhancing dopant, and the PMOS source/drain regions would comprise an appropriate p-type conductivity-enhancing dopant.

The lines 108, 110 and 112 are shown comprising constructions similar to those described above relative to line 14 of FIG. 2. Accordingly, the lines 108, 110 and 112 comprise a lower insulative material 120 and an upper insulative material 124. The lines further comprise conductive materials between the upper and lower insulative materials, with the conductive material of line 108 being labeled 122, the conductive material of line 110 being labeled 128, and the conductive material of line 112 being labeled 130. Insulative materials 120 and 124 can comprise the same materials as discussed above relative to insulative materials 22 and 26, respectively, of FIG. 2. Conductive materials 122, 128 and 130 can comprise the same conductive materials discussed above for conductive material 24 of FIG. 2, and can comprise the same conductive materials as one another, or can comprise different materials relative to one another.

FIG. 17 shows sidewall spacers 126 adjacent sidewalls of lines 108, 110 and 112. The sidewall spacers can comprises the same materials as the spacers 28 of FIG. 2. The spacers 126 are not shown in FIG. 16 to simplify the drawing.

Isolation regions 140 extend within base 102. Regions 140 can correspond to shallow trench isolation regions, and accordingly can comprise, consist essentially of, or consist of silicon dioxide. The middle isolation region 140 of FIG. 17 electrically isolates an active region associated with line 108 (the active region 114 of FIG. 16) from an active region associated with line 110 (the active region 116 of FIG. 16). Isolation regions 140 are not shown in the top view of FIG. 16 in order to simplify the drawing.

For purposes of the discussion that follows, line 108 can be referred to as a first conductive line and line 110 as a second conductive line. The sides 107 and 109 of line 108 can be referred to as first and second sides of line 108, respectively; and the sides 111 and 113 can be referred to as first and second sides of line 110, respectively. The NMOS source/drain regions formed along first side 107 (such as, for example, region 134 of FIG. 17) can be referred to as first NMOS source/drain regions, and the NMOS source/drain regions formed along the second side 109 (such as, for example, the region 132 of FIG. 17) can be referred to as second NMOS source/drain diffusion regions. The PMOS source/drain diffusion regions formed along the first side 111 of line 110 (such as, for example, the diffusion region 136 of FIG. 17) can be referred to as first PMOS source/drain diffusion regions, and the PMOS source/drain diffusion regions formed along the second side 113 of line 110 (such as the region 138 of FIG. 17) can be referred to as second PMOS source/drain diffusion regions.

Figure 19:
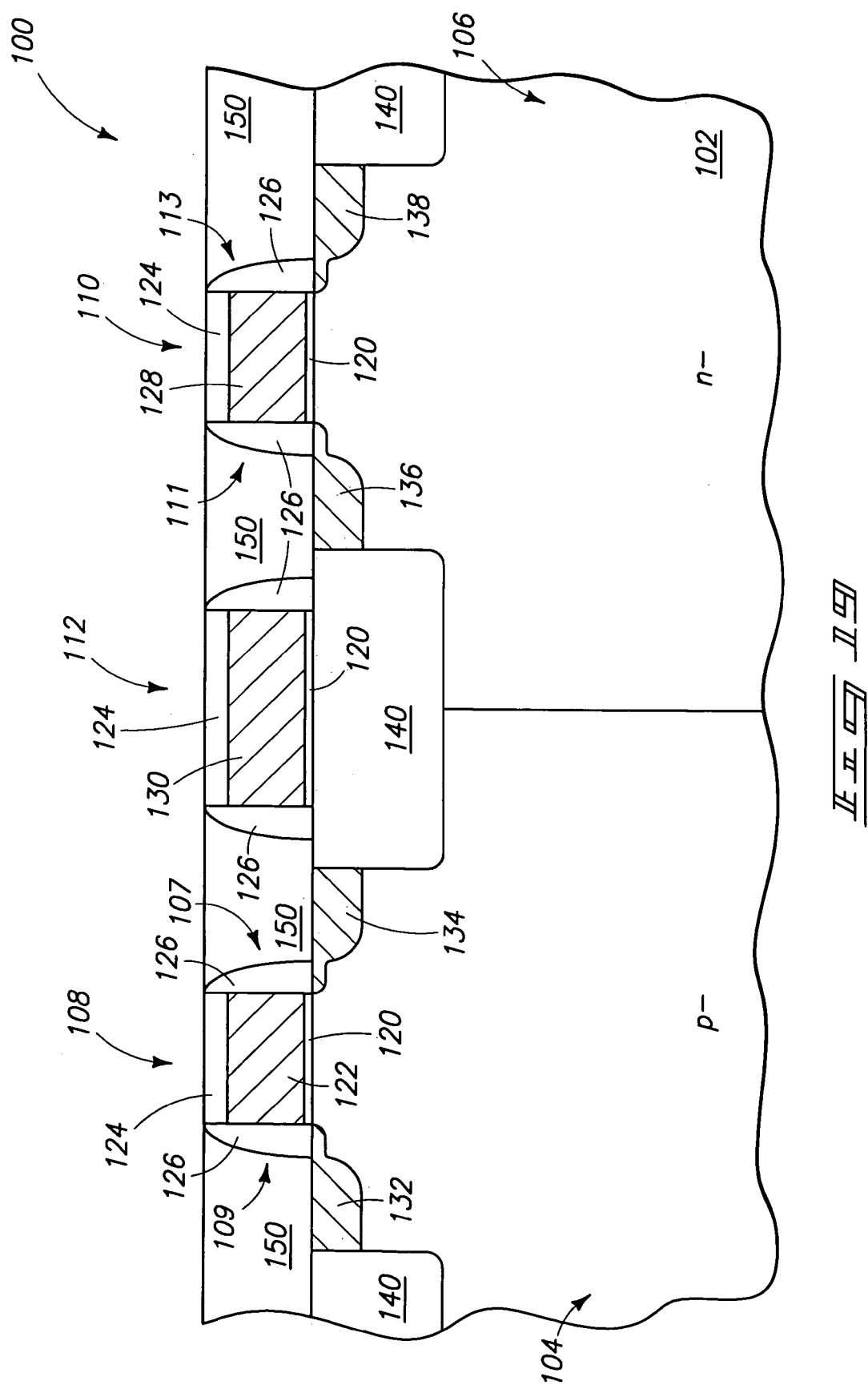

Referring next to FIGS. 18 and 19 an insulative material 150 is formed over base 100. Insulative material 150 can comprise an identical composition as described previously relative to insulative material 50 of FIG. 5. Insulative material 150 is shown comprising a planarized upper surface which is substantially coplanar with upper surfaces of insulative material 124 of lines 108, 110 and 112. Such can be accomplished by forming material 150 to extend across the uppermost surfaces of lines 108, 110 and 112 (i.e., over insulative material 124), and subsequently planarizing material 150 to remove the material from over the lines 108, 110 and 112. Such planarization can be accomplished by, for example, chemical-mechanical polishing.

The active regions 114 and 116 are shown in dashed line in FIG. 18 to emphasize that the active regions are beneath insulative material 150. The lines 135 and 137 utilized in FIG. 16 to demarcate separate source/drain regions are not shown in FIG. 18 in order to simplify the drawing.

Figure 20:
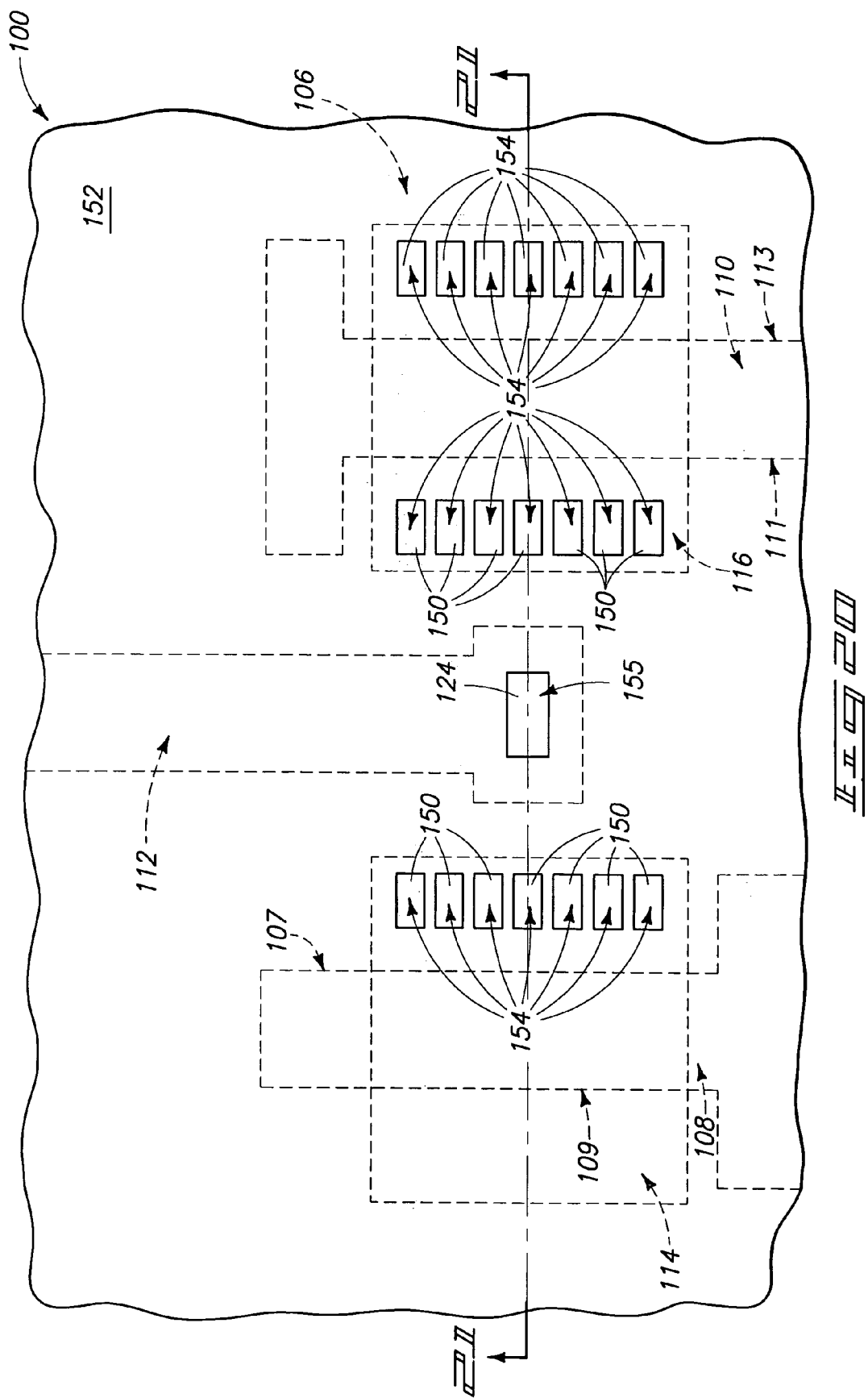

Referring next to FIGS. 20 and 21 a patterned layer 152 is formed over insulative material 150. Patterned material 152 can comprise the same composition discussed previously for material 52 of FIG. 5. Accordingly, patterned material 152 can comprise, consist essentially of, or consist of silicon and one or both of oxygen and nitrogen. A pattern can be formed in material 152 utilizing, for example, photolithographic processing and an appropriate etch, as discussed previously for forming a pattern in material 52 of FIG. 5. A series of openings 154 extend through material 152, and an opening 155 also extends through material 152. The openings 154 are directly over NMOS source/drain regions along the first side 107 of line 108, and over the PMOS source/drain regions along the first and second sides 111 and 113 of line 110. The opening 155 is over line 112. In alternative processing, the opening over line 112 can be formed at different processing stage than the openings over the source/drain regions.

The openings 154 can be, in particular aspects, considered to comprise a first set in one-to-one correspondence with the NMOS source/drain diffusion regions along the first side of the conductive line 108, a second set in one-to-one correspondence with the PMOS source/drain regions along the first side of conductive line 112, and a third set in one-to-one correspondence with the PMOS source/drain regions along the second side of line 112.

The shown pattern of openings 154 within layer 152 does not include any openings over the NMOS diffusion regions along the second side 109 of line 108.

Although a plurality of openings 154 are shown formed over the series of NMOS diffusion regions, it is to be understood that a single opening could be formed over all of the source/drain regions. Such opening would have the form of a trench extending the length of the active region along side 107 of line 108. Similarly, the plurality of openings 154 extending along the sides 111 and 113 of line 112 could be replaced with a trench-like opening along the side 111 of line 112, and another trench-like opening extending along the side 113 of line 112. Patterned layer 152 can be referred to as an etch stop, for reasons similar to those discussed above relative to layer 52 of FIG. 5.

The opening 155 is shown extending through layer 124 and to conductive material 130 of line 112. Such can be accomplished with a suitable etch of material 124, and in some aspects the etch of material 124 utilizes the same etch as is utilized for patterning layer 152.

Figure 23:
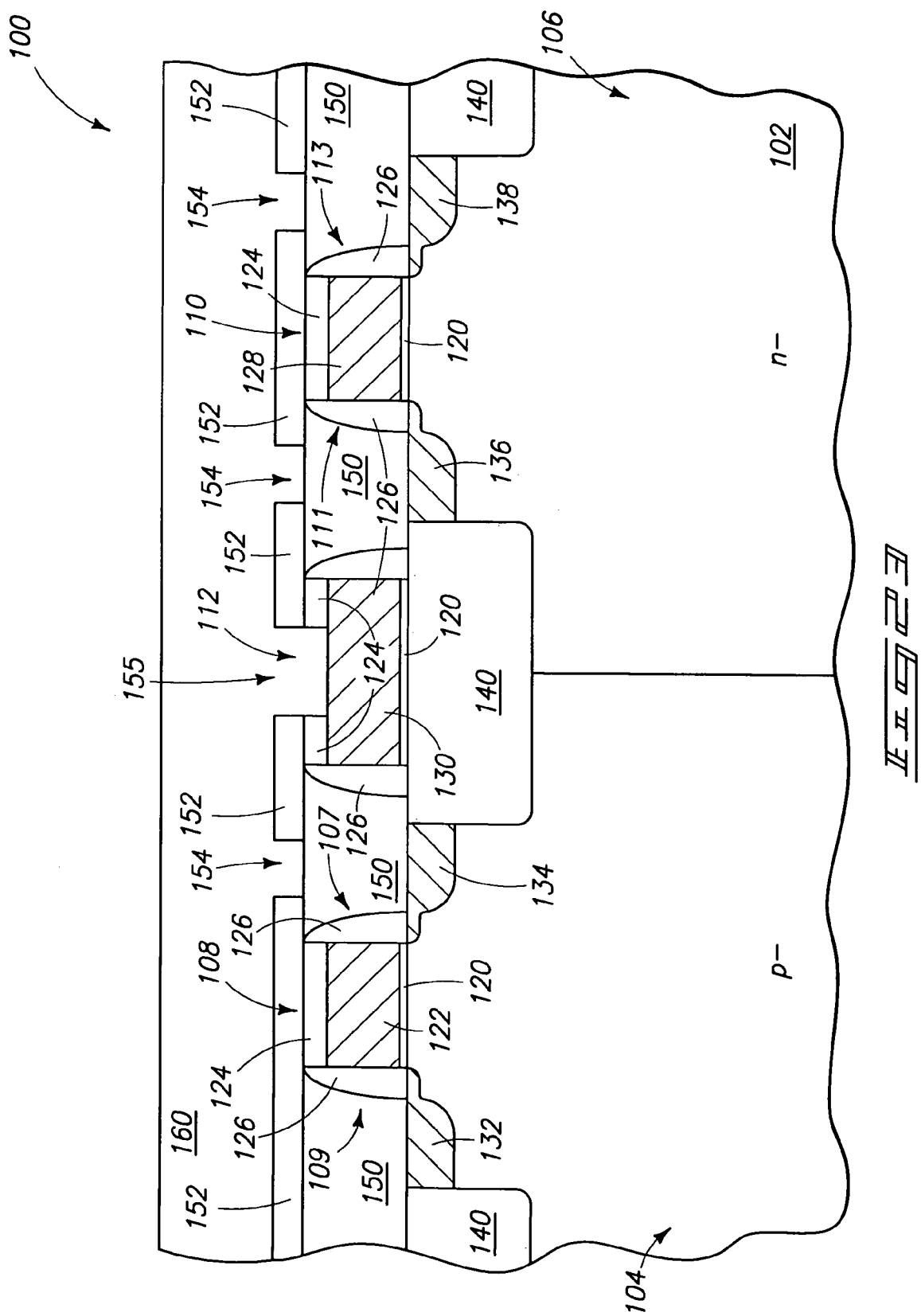

Referring to FIGS. 22 and 23, an electrically insulative material 160 is formed over patterned layer 152, and within the openings 154 and 155 extending through patterned layer 152. The insulative material 160 can comprise the same compositions as discussed previously for insulative material 60 of FIGS. 7–9. Accordingly, the insulative material 160 can comprise an identical composition as the insulative material 150, and in particular aspects both insulative materials can comprise, consist essentially of, or consist of doped oxide. Insulative materials 150 and 160 can be referred to as a first insulative material and a second insulative material, respectively, to distinguish the materials from one another.

Figure 24:
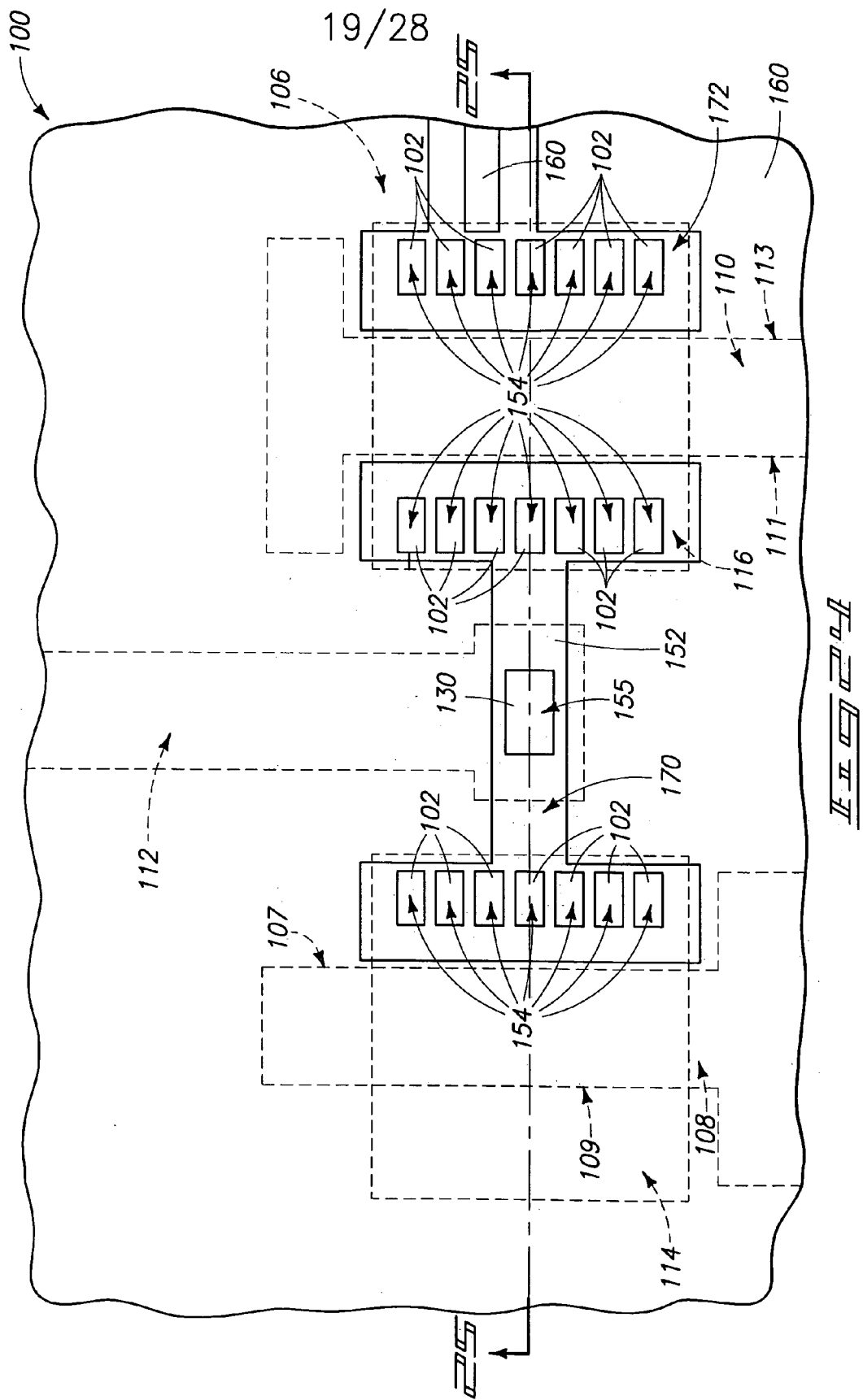
FIGS. 24 and 25 are views of the fragments of FIGS. 16 and 17, respectively, shown at a processing stage subsequent to that of FIGS. 22 and 23. The cross-section of FIG. 25 is along the line 25—25 of FIG. 24.
Figure 25:
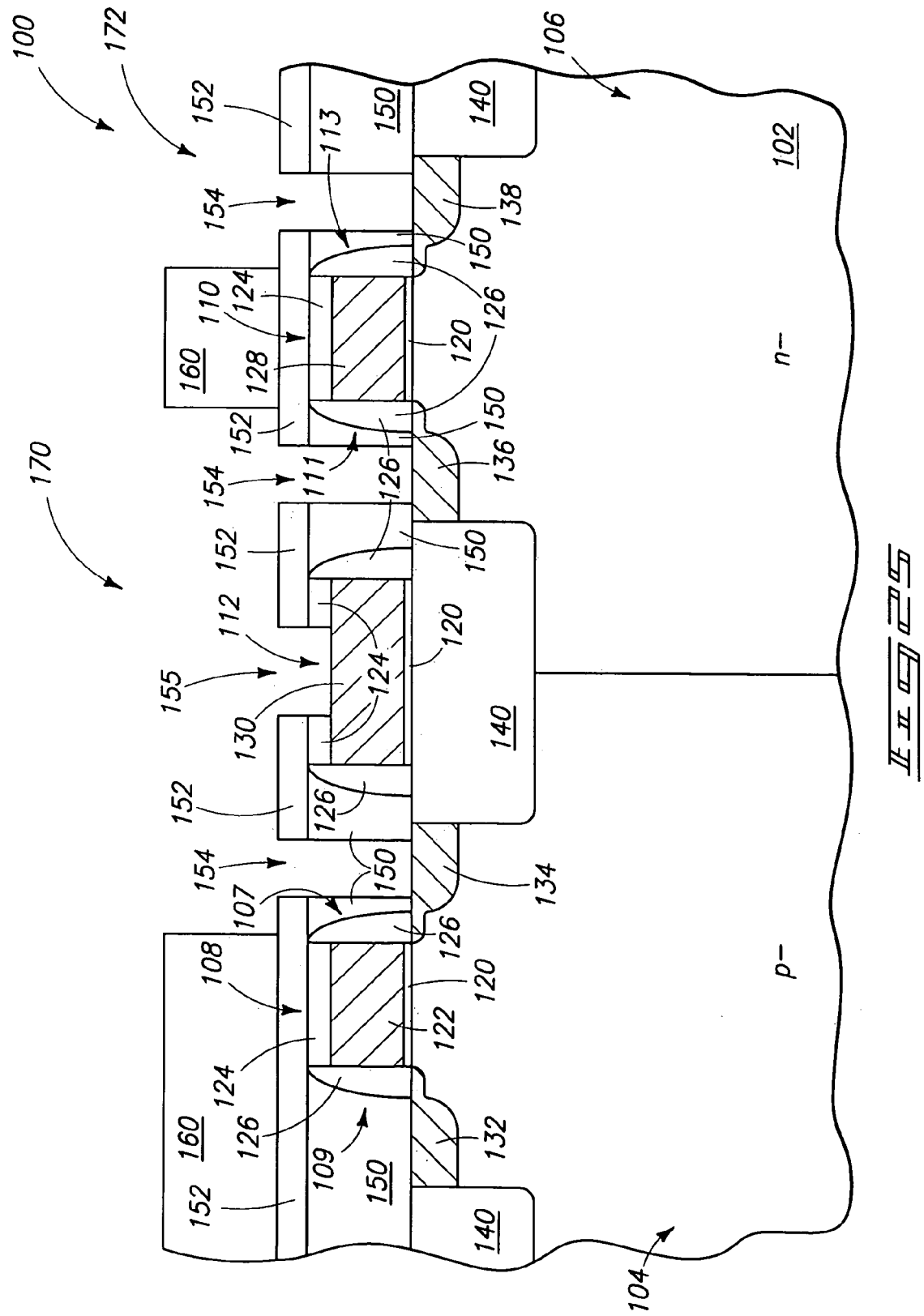

Referring next to FIGS. 24 and 25, a pair of trenches 170 and 172 are formed within second insulative material 160. The trenches 170 and 172 can be referred to as a first trench and second trench, respectively. It is noted that FIG. 25 is drawn to show only those materials which are along the plane of the cross-section, rather than materials out of the plane, to simplify the drawing.

The etching utilized to form the trenches 170 and 172 is selective for material 160 relative to material 152, and accordingly substantially stops on layer 152. In subsequent etching, or continuation of the same etching, regions of insulative material 150 exposed through openings 154 are removed to extend the openings to base 102. The etching utilized to extend the openings 154 is preferably selective for material 150 relative to material 152. The openings 154 extending through material 150 to base 102 extend to conductively-doped diffusion regions within the NMOS active region 114 (such as diffusion region 134) and the PMOS active region 116 (such as diffusion regions 136 and 138). The openings can extend entirely to the diffusion regions (as shown), or can extend to proximate the diffusion regions in, for example, an application such as that described below with reference to FIG. 32 wherein a conductive material is over the diffusion regions.

The first trench 170 has a portion directly over the NMOS diffusion regions along the first side 107 of line 108 (and specifically directly over the openings 154 that are directly over such NMOS diffusion regions). The first trench also has a portion directly over the PMOS diffusion regions along the side 111 of line 110 (and specifically directly over the openings 154 that are directly over such PMOS diffusion regions). Additionally, the first trench has a portion directly over an opening 154 extending to the conductive material 130 of line 112.

The second trench 172 comprises a portion directly over the PMOS diffusion regions along side 113 of line 110 (and specifically directly over the openings 154 that are directly over such PMOS diffusion regions).

Although only two trenches are shown formed, it is to be understood that the invention encompasses other aspects wherein more than two trenches are simultaneously formed.

Figure 26:
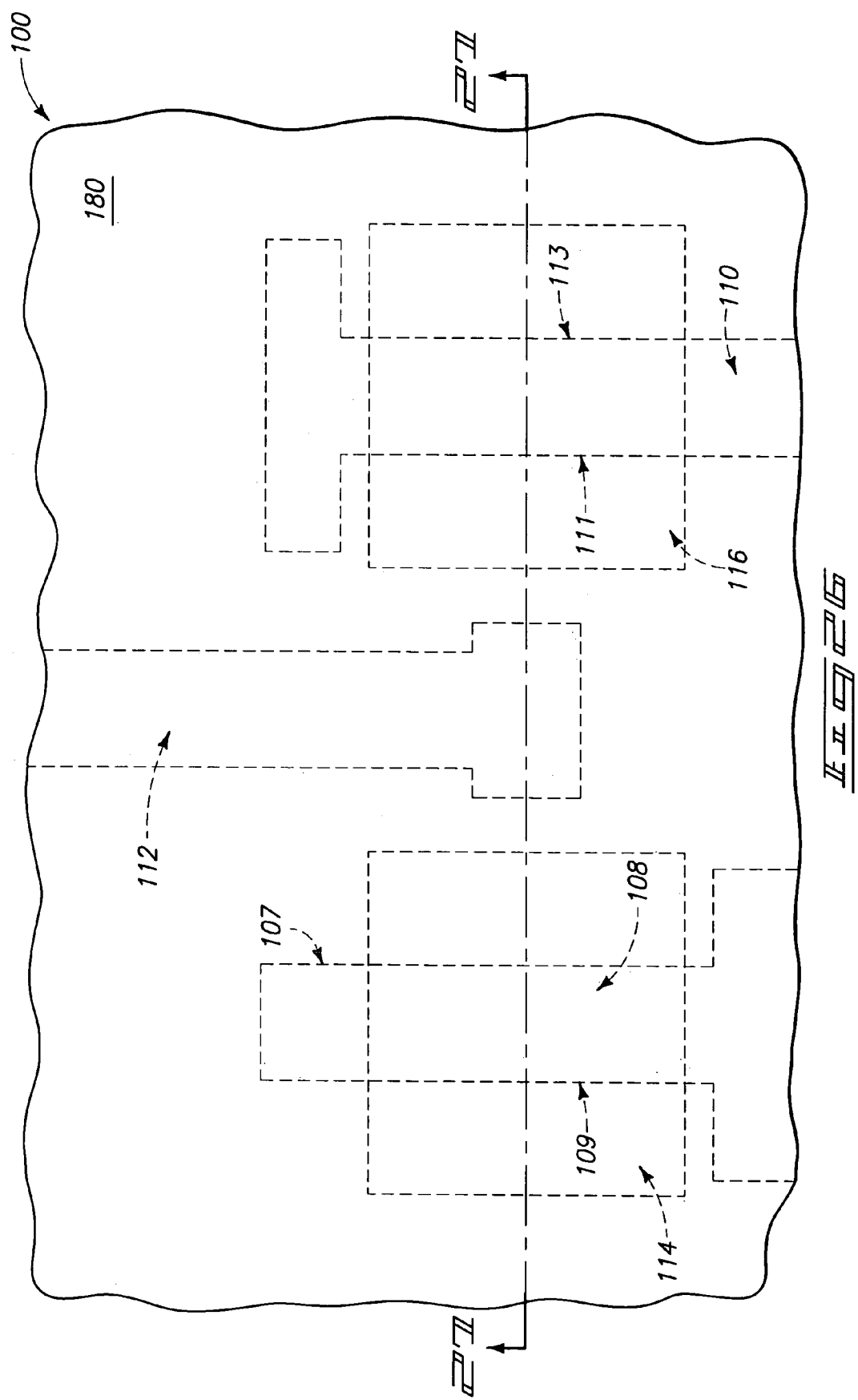
FIGS. 26 and 27 are views of the fragments of FIGS. 16 and 17, respectively, shown at a processing stage subsequent to that of FIGS. 24 and 25. The cross-section of FIG. 27 is along the line 27—27 of FIG. 26.
Figure 27:
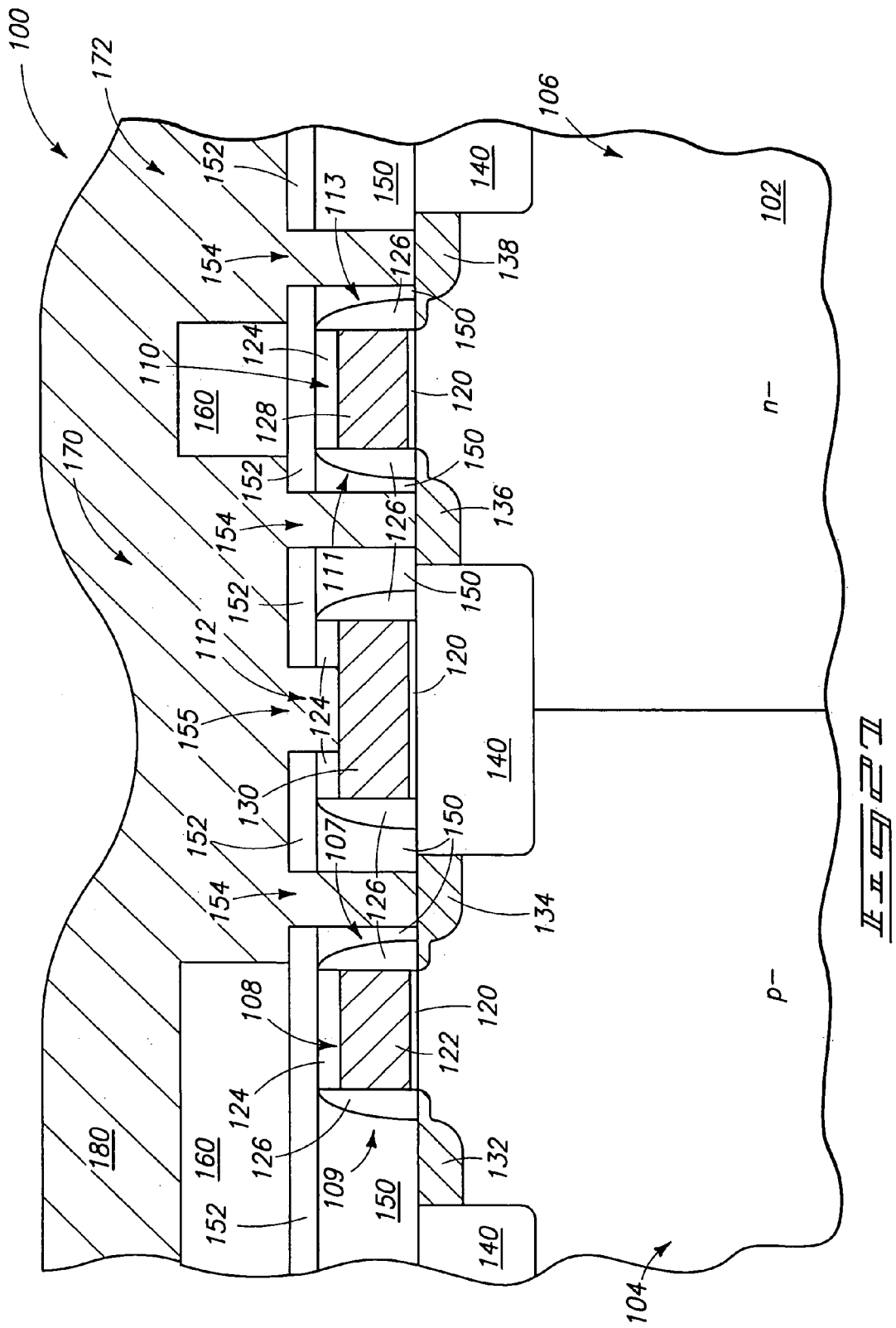

Referring next to FIGS. 26 and 27, a conductive material 180 is formed over insulative material 160, within openings 154, and within trenches 170 and 172. Conductive material 180 can comprise any suitable composition, or combination of compositions. For instance, conductive material 180 can comprise a refractive metal; and in particular aspects can comprise a thin layer of metal nitride (such as, for example, titanium nitride or tungsten nitride), and a thick layer of tungsten. As another example, material 180 can comprise a layer comprising, consisting essentially of, or consisting of copper. The copper-containing layer can be utilized together with one or more copper diffusion barrier layers which protect active areas from copper contamination. Lines 108, 110 and 112, together with active regions 114 and 116, are shown in phantom view in FIG. 26 to indicate that such are beneath the material 180.

Figure 28:
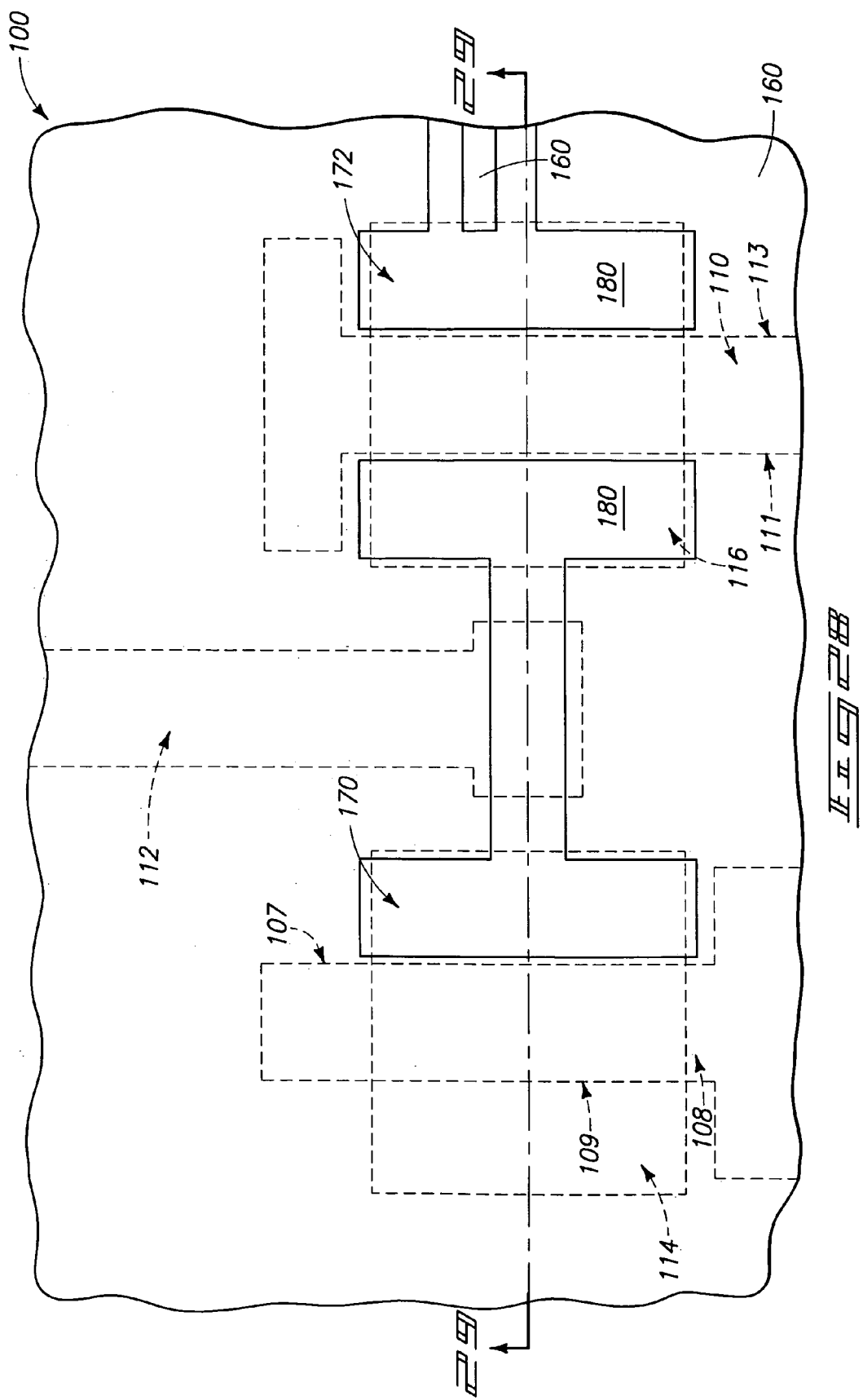
FIGS. 28 and 29 are views of the fragments of FIGS. 16 and 17, respectively, shown at a processing stage subsequent to that of FIGS. 26 and 27. The cross-section of FIG. 29 is along the line 29—29 of FIG. 28.
Figure 29:
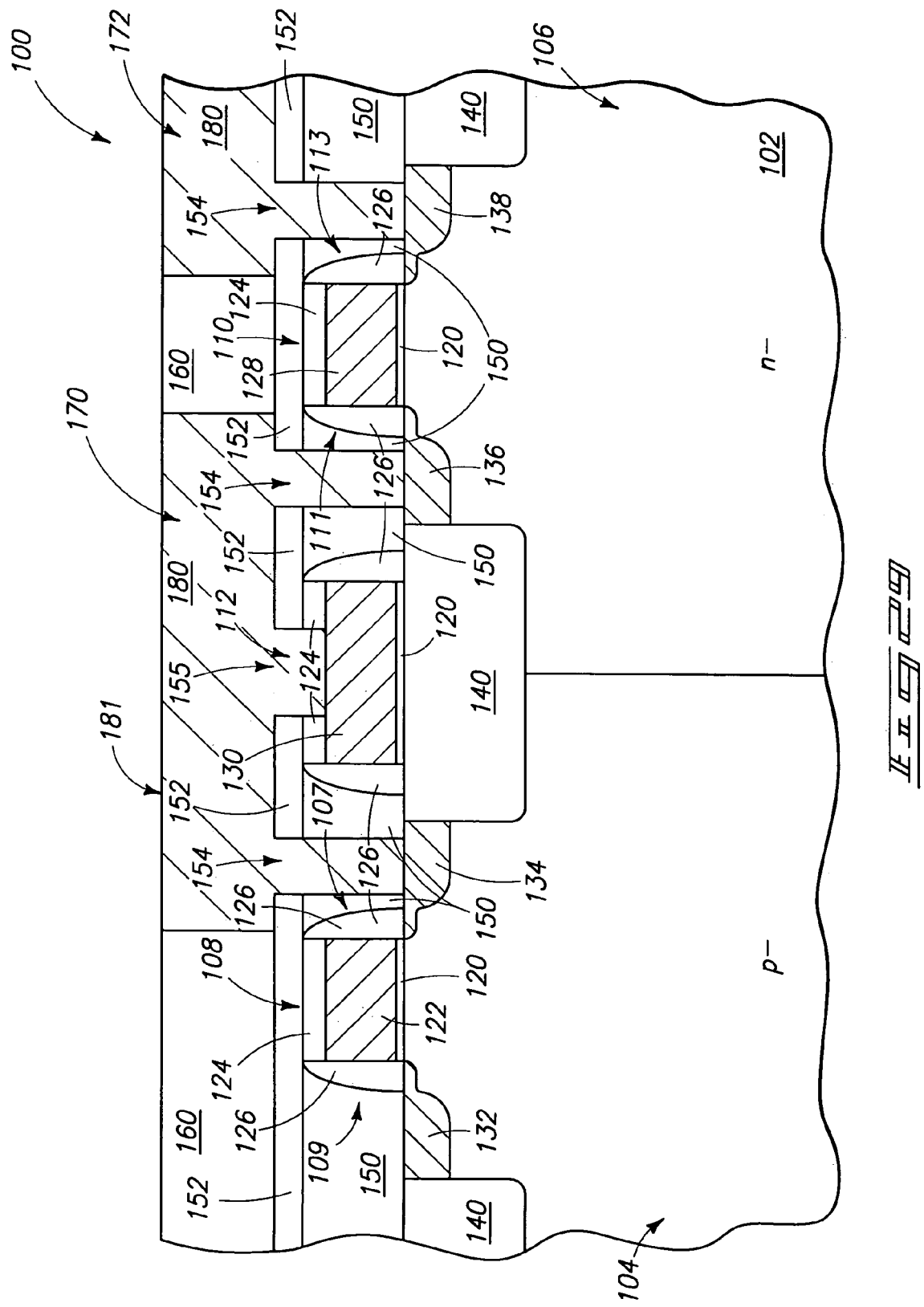

Referring next to FIGS. 28 and 29, material 180 is subjected to planarization to form a planarized upper surface 181 across the material, and to remove the material from over insulative material 160. Suitable planarization can be accomplished utilizing, for example, chemical-mechanical polishing. The planarization may, in particular aspects, remove some of material 160 so that an upper elevational level of the material 160 at the processing stage of FIG. 29 is beneath that at the processing stage of FIG. 27.

The removal of material 180 from over the upper surface of material 160 electrically isolates the material 180 within trench 170 from the material 180 within the trench 172. The material 180 within trench 170 electrically connects NMOS source/drain regions along first side 107 of line 108 with PMOS source/drain regions along first side 111 of line 110. The conductive material 180 further connects the NMOS and PMOS source/drain regions to electrically conductive material 130 of line 112 (i.e., forms a gate over field or transistor gate connection).

Figure 30:
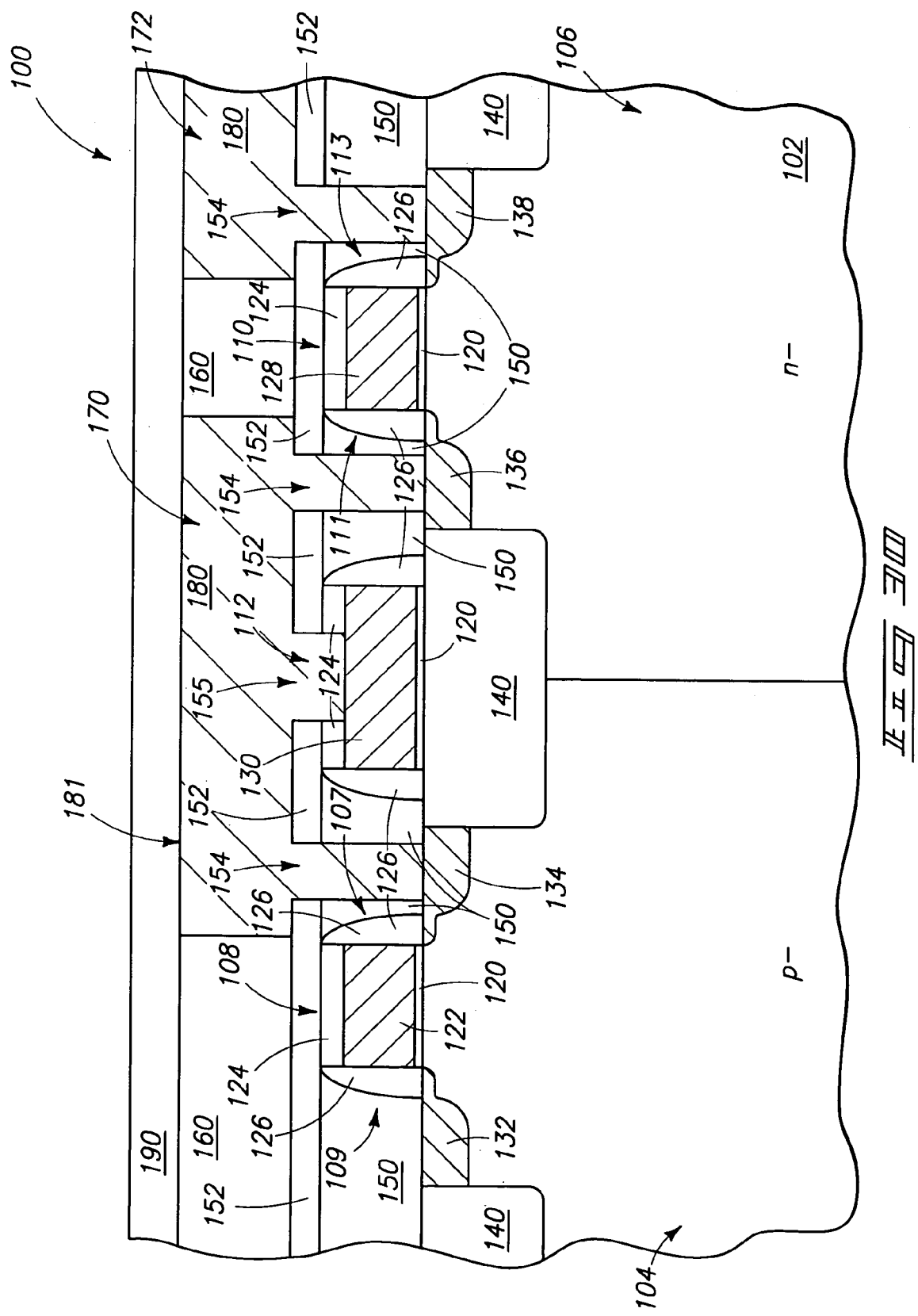
FIG. 30 is a view of the FIG. 17 wafer fragment at a processing stage subsequent to that of FIG. 29.

Referring next to FIG. 30, an electrically insulative cap 190 is formed over planarized upper surface 181 of material 180 and insulative material 160. Cap 190 can comprise any suitable electrically insulative material, including, for example, silicon nitride.

The construction of FIG. 30 can be incorporated into numerous CMOS structures, including, for example, CMOS inverters and static random access memory (SRAM) cells; and/or can be incorporated into repeated logic cells such as shift registers or arithmetic units. Also, the construction can be incorporated into applications in which dynamic random access memory (DRAM) and SRAM are integrated into a common circuit. The construction can, for example, be incorporated into system-on-chip (SOC) integration, digital signal processing (DSP), microprocessors and embedded application specific integrated circuit (ASIC) chips.

Figure 31:
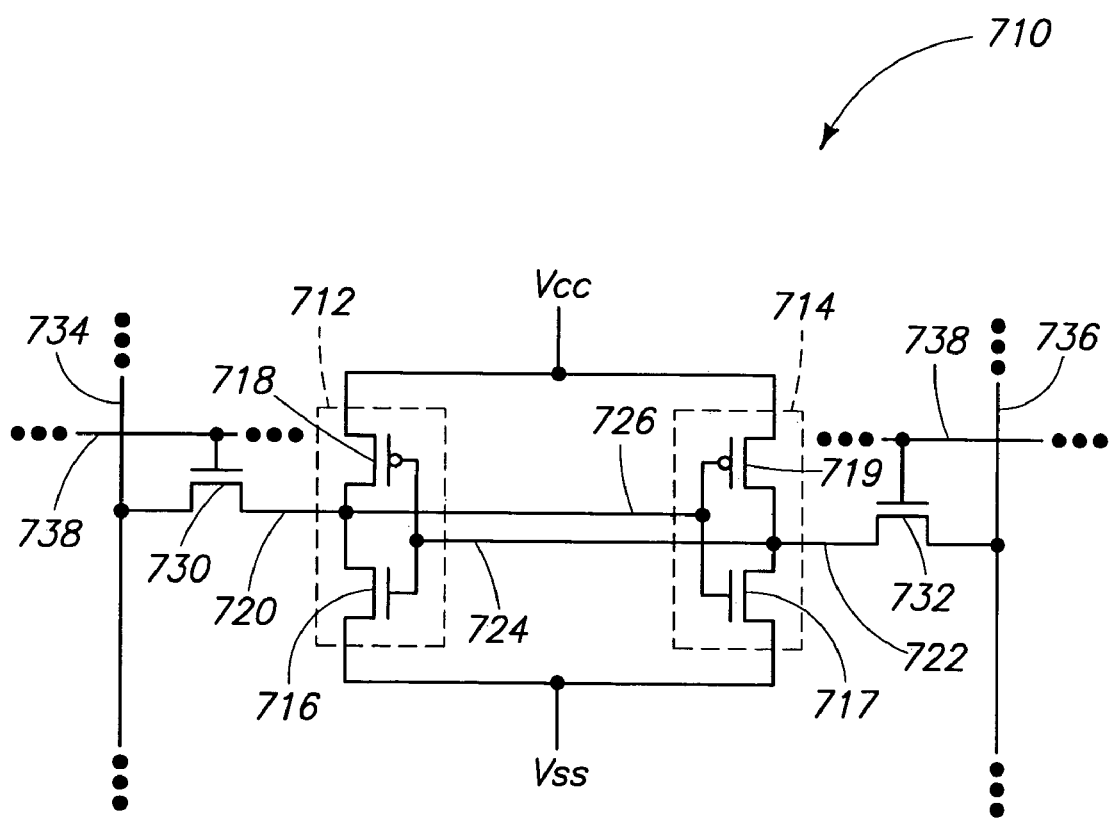
FIG. 31 is a diagrammatic, schematic illustration of a prior art SRAM cell.

FIG. 31 shows a diagrammatic illustration of a prior art six transistor SRAM cell 710. The cell comprises first and second inverters 712 and 714 which are cross-coupled to form a bistable flip-flop. Inverters 712 and 714 are formed by n-channel driver transistors 716 and 717, and p-channel load transistors 718 and 719. The source regions of driver transistors 716 and 717 are tied to a low reference or circuit supply voltage, labeled $V_{ss}$ and typically referred to as "ground". Load transistors 718 and 719 are connected in series between a high reference or circuit supply voltage, labeled $V_{cc}$, and the drains of corresponding driver transistors 716 and 717. The gates of load transistors 718 and 719 are connected to the gates of the corresponding driver transistors 716 and 717.

Inverter 712 has an inverter output 720 formed by the drain of device transistor 716, and similarly inverter 714 has an inverter output 722 formed by the drain of driver transistor 717. Inverter 712 has an inverter input 724 formed by the gate of driver transistor 716, and inverter 714 has an inverter input 726 formed by the gate of device transistor 717. The inputs and outputs of inverter 712 and 714 are cross-coupled to form a flip-flop having a pair of complementary two-state outputs. Specifically, inverter output 720 is cross-coupled to inverter input 726, and inverter output 722 is cross-coupled to inverter input 724. In this configuration, inverter outputs 720 and 722 form the complementary two-state outputs of the flip-flop.

A memory flip-flop such as that described typically forms one memory element of an integrated array of static memory elements. A plurality of access transistors, such as access transistor 730 and 732, are used to selectively address and access individual memory elements within the array. Access transistor 730 has one active terminal connected to cross-coupled inverter output 720. Access transistor 732 has one active terminal connected to cross-coupled inverter output 722. A plurality of complementary column line pairs, such as the single pair of complementary column lines 734 and 736 shown, are connected to the remaining active terminals of access transistors 730 and 732, respectively. A row line 738 is connected to the gates of access transistors 730 and 732.

Reading static memory cell 710 involves activating row line 738 to connect to inverter outputs 720 and 722 to column lines 734 and 736. Writing to static memory cell 710 involves first placing selective complementary logic voltages on column lines 734 and 736, and then activating row line 738 to connect those logic voltages to inverter outputs 720 and 722. This forces the outputs to the selected logic voltages, which will be maintained as long as power is supplied to the memory cell, or until the memory cell is reprogrammed.

The structure of FIG. 30 can be incorporated into a SRAM cell of the type shown in FIG. 31.

Referring next to FIG. 32, an aspect of the invention alternative to that of FIG. 29 is illustrated with reference to a semiconductor wafer fragment 200. Several components of wafer fragment 200 are identical to those shown in FIG. 29, and such components will be labeled identically to the labeling used with reference to FIG. 29. A difference between the fragment 200 of FIG. 32 and the fragment 100 of FIG. 29 is that there is no opening extending to the conductive material 130 of line 112. Instead, patterned material 152 is formed to entirely cover line 112 so that there was no opening to be extending to the conductive material 130 at a processing stage analogous to that described with reference to FIGS. 20 and 21. If an electrical connection between conductive material 180 and the material 130 of line 112 is desired, such can be formed with additional processing steps.

Another difference between structure 200 of FIG. 32 and the structure 100 of FIG. 29 is that the structure 200 has conductive pedestals 202 over the NMOS and PMOS source/drain regions. The conductive pedestals can comprise any suitable material, including, for example, epitaxially-grown silicon and/or metals and/or metal silicide compounds. Pedestals 202 can be provided prior to formation of insulative material 150 (FIG. 19), and accordingly the step of extending openings through material 150 and toward diffusion regions underlying material 150 (such as processing analogous to that described above with reference to FIG. 25) can be conducted to extend the openings to upper surfaces of pedestals 202, or at least to proximate such upper surfaces so that conductive material 180 will be formed to be electrically connected with pedestals 202. The electrical connection of material 180 with pedestals 202 is also electrical connection to the diffusion regions underlying the pedestals 202, in that the pedestals 202 are electrically connected with such diffusion regions.

The invention described herein can be utilized for numerous applications in which it is desired to connect (i.e. strap) active areas to one another. The invention can be utilized for strapping PMOS regions to NMOS regions, or can be utilized in connecting PMOS regions with one another and/or interconnecting NMOS regions with one another. Various aspects of the invention utilize a trench etch aligned with etching through openings underlying the trench to desired regions. The devices formed utilizing methodology of the present invention can be appropriately shunted for low parasitic resistance, and the methodology of the present invention can be utilized for forming interconnects with fewer masking steps than would be utilized with other methodologies. The invention can, in particular aspects, allow strapping of source/drain regions of transistors utilizing lower sheet resistance materials than are utilized with other methodologies. The height of the conducting interconnect material can be adjusted by adjusting trench depth, and the amount of etch back. Methodology of the present invention can be utilized for providing various interconnects without additional masking steps that would conventionally be utilized. Additionally, methodology of the present invention can allow thinner conductive materials to be utilized in a memory region (such as a region comprising an SRAM) then in a region peripheral to the memory region, and can allow utilization of low-k dielectric materials for reduced cross-coupling capacitance within both a memory array and a region peripheral to the memory array.

Methodology of the present invention can be utilized for numerous applications, including applications where tight pitch metal bitlines are used. Methodology of the present invention can, for instance, be utilized in forming numerous memory storage and/or logic devices, including, for example, DRAM arrays, SRAM arrays, flash memory arrays, non-volatile memory arrays and phase change memory arrays.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of forming an electrical connection for a semiconductor construction, comprising:
   providing a semiconductor substrate having a conductive line thereover and having one or more diffusion regions therein and adjacent the conductive line, the line extending along a first axis;
   forming a patterned layer over said one or more diffusion regions, the patterned layer having a plurality of openings extending therein, at least some of the openings being along a row extending along a second axis substantially parallel to the first axis and being directly over at least one of said one or more diffusion regions;
   forming an electrically insulative material over the patterned layer;
   exposing the electrically insulative material to an etch which forms a trench extending through the electrically insulative material to the patterned layer, to two or more of the plurality of openings, and which extends at least some of the openings along said row toward the at least one of said one or more diffusion regions, the etch being selective for removing the electrically insulative material relative to the patterned layer, at least a portion of the trench being directly over the openings and extending along the second axis; and
   forming an electrically conductive material within the openings and within the trench, the electrically conductive material being in electrical connection with the at least one of said one or more diffusion regions.

2. The method of claim 1 further comprising incorporating said at least one of the one or more diffusion regions and the conductive material into a DRAM array.

3. The method of claim 1 further comprising incorporating said at least one of the one or more diffusion regions and the conductive material into an SRAM array.

4. The method of claim 1 further comprising incorporating said at least one of the one or more diffusion regions and the conductive material into a flash memory array.

5. The method of claim 1 further comprising incorporating said at least one of the one or more diffusion regions and the conductive material into a non-volatile memory array.

6. The method of claim 1 further comprising incorporating said at least one of the one or more diffusion regions and the conductive material into a phase change memory array.

7. The method of claim 1 wherein the openings are extended to more than one of the one or more diffusion regions.

8. The method of claim 1 further comprising at least one conductive structure over and in electrical contact with said at least one of the one or more diffusion regions, and wherein the openings are extended to the at least one conductive structure.

9. The method of claim 1 wherein the electrically insulative material is a second electrically insulative material, and further comprising:
   forming a first electrically insulative material over said one or more diffusion regions;
   forming the patterned layer over the first electrically insulative material; and
   wherein the etch etches through the second electrically insulative material to form the trench and etches into the first electrically insulative material to extend the openings.

10. The method of claim 9 wherein the first electrically insulative material consists of a composition and wherein the second electrically insulative material also consists of the composition.

11. The method of claim 10 wherein the composition is a doped silicon oxide.

12. The method of claim 1 wherein the one or more diffusion regions are more than one diffusion region.

13. The method of claim 1 wherein the patterned layer comprises silicon and one or both of oxygen and nitrogen.

14. The method of claim 1 wherein the patterned layer consists essentially of silicon and one or both of oxygen and nitrogen.

15. The method of claim 1 wherein the patterned layer consists of silicon and one or both of oxygen and nitrogen.

16. The method of claim 15 wherein the electrically insulative material consists of a doped silicon oxide.

17. The method of claim 1 wherein the patterned layer comprises silicon dioxide.

18. The method of claim 1 wherein the patterned layer comprises silicon nitride.

19. The method of claim 1 wherein the patterned layer comprises silicon oxynitride.

20. The method of claim 1 wherein the conductive line has a pair of opposing sides, the opposing sides being a first side and a second side; wherein said one or more diffusion regions are along the first side, wherein the row of openings extending through the patterned layer is a first row, and wherein the trench is a first trench, the method further comprising:
   forming at least one second diffusion region within the substrate along the second side of the conductive line;
   forming the patterned layer to have at least some of the openings extending therethrough along a second row extending along a third axis substantially parallel to the first axis and being directly over the at least one second diffusion region; the openings directly over the at least one second diffusion region being second openings;
   the exposure of the electrically insulative material to the etch forming a second trench extending through the second electrically insulative material to the patterned layer and extending said second openings toward the at least one second diffusion region, at least a portion of the second trench being directly over the second openings and extending along the third axis; and forming the electrically conductive material within the second openings and within the second trench.

21. The method of claim 20 wherein the electrically conductive material within the first trench is electrically isolated from the electrically conductive material within the second trench.

22. The method of claim 20 wherein the at least one first diffusion region is a single first diffusion region and wherein the at least one second diffusion region is a single second diffusion region.

23. The method of claim 22 wherein the single first diffusion region is connected to the single second diffusion region through a transistor gate comprised by the conductive line.

24. The method of claim 20 wherein the at least one first diffusion region is a plurality of first diffusion regions, and wherein the at least one second diffusion region is a plurality of second diffusion regions.

25. The method of claim 24 wherein the first diffusion regions are connected to the second diffusion regions through a plurality of transistor gates comprised by the conductive line.

26. A method of forming an electrical connection to a plurality of source/drain regions, comprising:

providing a semiconductor substrate;

providing a wordline over the substrate, the wordline having a pair of opposing sides;

providing a plurality of source/drain diffusion regions within the substrate and along one of the sides of the wordline;

forming a first electrically insulative material over the source/drain diffusion regions;

forming a patterned etch stop over the first electrically insulative material, the patterned etch stop having at least one opening extending therethrough, the at least one opening being directly over two or more of the source/drain diffusion regions;

forming a second electrically insulative material over the patterned etch stop;

etching the first and second electrically insulative materials to form a trench extending through the second electrically insulative material to the patterned etch stop and to extend the at least one opening within the patterned etch stop into the first electrically insulative material, at least a portion of the trench being directly over the openings; and forming an electrically conductive material within the at least one opening and within the trench, the electrically conductive material being in electrical connection with the two or more source/drain diffusion regions.

27. The method of claim 26 wherein said at least one opening includes a single opening directly over at least two of the source/drain diffusion regions.

28. The method of claim 26 wherein the patterned etch stop comprises silicon and one or both of oxygen and nitrogen.

29. The method of claim 26 wherein the patterned etch stop consists essentially of silicon and one or both of oxygen and nitrogen.

30. The method of claim 26 wherein the patterned etch stop consists of silicon and one or both of oxygen and nitrogen.

31. The method of claim 26 wherein the patterned etch stop comprises silicon dioxide.

32. The method of claim 26 wherein the patterned etch stop comprises silicon nitride.

33. The method of claim 26 wherein the patterned etch stop comprises silicon oxynitride.

34. The method of claim 26 wherein the first electrically insulative material consists of a composition and wherein the second electrically insulative material also consists of the composition.

35. The method of claim 34 wherein the composition is a doped silicon oxide, and wherein the patterned etch stop consists of silicon and one or both of oxygen and nitrogen.

36. A method of forming an electrical connection to a plurality of source/drain regions, comprising:

providing a semiconductor substrate;

providing a wordline over the substrate, the wordline having a pair of opposing sides;

providing a plurality of source/drain diffusion regions within the substrate and along one of the sides of the wordline;

forming a first electrically insulative material over the source/drain diffusion regions;

forming a patterned etch stop over the first electrically insulative material, the patterned etch stop having a plurality of openings extending there through, at least some of the openings being directly over at least some of the source/drain diffusion regions;

forming a second electrically insulative material over the patterned etch stop;

etching the first and second electrically insulative materials to form a trench extending through the second electrically insulative material to the patterned etch stop and to extend the at least some of openings within the patterned etch stop into the first electrically insulative material, at least a portion of the trench being directly over the openings; and forming an electrically conductive material within the openings and within the trench, the electrically conductive material being in electrical connection with the source/drain diffusion regions.

37. The method of claim 36 wherein the openings are extended to the source/drain diffusion regions.

38. The method of claim 36 wherein the source/drain diffusion regions are electrically connected to conductive pedestals that are over the source/drain diffusion regions, and wherein the openings are extended to the conductive pedestals.

39. The method of claim 36 wherein the patterned etch stop comprises silicon and one or both of oxygen and nitrogen.

40. The method of claim 36 wherein the patterned etch stop consists essentially of silicon and one or both of oxygen and nitrogen.

41. The method of claim 36 wherein the patterned etch stop consists of silicon and one or both of oxygen and nitrogen.

42. The method of claim 36 wherein the patterned etch stop comprises silicon dioxide.

43. The method of claim 36 wherein the patterned etch stop comprises silicon nitride.

44. The method of claim 36 wherein the patterned etch stop comprises silicon oxynitride.

45. The method of claim 36 wherein the first electrically insulative material consists of a composition and wherein the second electrically insulative material also consists of the composition.

46. The method of claim 45 wherein the composition is a doped silicon oxide, and wherein the patterned etch stop consists of silicon and one or both of oxygen and nitrogen.

47. The method of claim 36 wherein the opposing sides of the wordline are a first side and a second side; wherein said one of the opposing sides is the first side, wherein said plurality of source/drain diffusion regions are first source/drain diffusion regions, and wherein the trench is a first trench, the method further comprising:
- forming a plurality of second source/drain diffusion regions within the substrate along the second side of the wordline;
- forming the first electrically insulative material over the second source/drain diffusion regions;
- forming the patterned etch stop to have at least some of the openings extending therethrough directly over at least some of the second source/drain regions; the openings directly over the second source/drain diffusion regions being second openings;
- etching the first and second electrically insulative materials to form a second trench extending through the second electrically insulative material to the patterned etch stop and to extend the second openings within the patterned etch stop into the first electrically insulative material, at least a portion of the second trench being directly over the second openings; and
- forming the electrically conductive material within the second openings, within the second trench, and in electrical connection with the second source/drain diffusion regions.

48. The method of claim 47 wherein the electrically conductive material within the first trench is electrically isolated from the electrically conductive material within the second trench.

49. The method of claim 47 wherein the second openings are extended to the second source/drain diffusion regions.

50. The method of claim 47 wherein the second source/drain diffusion regions are electrically connected to conductive pedestals that are over the second source/drain diffusion regions, and wherein the second openings are extended to the conductive pedestals.

* * * * *

UNITED STATES PATENT AND TRADEMARK OFFICE
CERTIFICATE OF CORRECTION

| | | |
|---|---|---|
| PATENT NO. | : 7,135,401 B2 | Page 1 of 1 |
| APPLICATION NO. | : 10/841708 | |
| DATED | : November 14, 2006 | |
| INVENTOR(S) | : Luan C. Tran | |

It is certified that error appears in the above-identified patent and that said Letters Patent is hereby corrected as shown below:

Col. 1, line 32 –
  Replace "Inventive aspects described herein can be particular useful"
  With --Inventive aspects described herein can be particularly useful--

Col. 3, line 53 –
  Replace "at a processing stage analogous to the that of FIG. 4 in"
  With --at a processing stage analogous to that of FIG. 4 in--

Col. 8, line 53 –
  Replace "example a wordline associate with a memory array. The"
  With --example, a wordline associated with a memory array. The--

Col. 9, line 28 –
  Replace "(shown as n- in FIG. 17). The n-region would typically be"
  With --(shown as n- in FIG. 17). The n- region would typically be--

Col. 10, line 31 –
  Replace "lines 108, 110 and 112. The sidewall spacers can comprises"
  With --lines 108, 110 and 112. The sidewall spacers can comprise--

Signed and Sealed this

Thirty-first Day of July, 2007

JON W. DUDAS
*Director of the United States Patent and Trademark Office*